United States Patent
Ito et al.

(10) Patent No.: US 10,252,136 B2
(45) Date of Patent: Apr. 9, 2019

(54) SWING DIAGNOSIS APPARATUS, SWING DIAGNOSIS SYSTEM, SWING DIAGNOSIS METHOD, AND RECORDING MEDIUM

(71) Applicant: SEIKO EPSON CORPORATION, Tokyo (JP)

(72) Inventors: Tsuyoshi Ito, Suwa (JP); Kenya Kodaira, Azumino (JP); Norihisa Hagiwara, Hachioji (JP); Kazuhiro Ito, Yokohama (JP)

(73) Assignee: SEIKO EPSON CORPORATION, Tokyo (JP)

( * ) Notice: Subject to any disclaimer, the term of this patent is extended or adjusted under 35 U.S.C. 154(b) by 370 days.

(21) Appl. No.: 15/211,490

(22) Filed: Jul. 15, 2016

(65) Prior Publication Data
US 2017/0028252 A1     Feb. 2, 2017

(30) Foreign Application Priority Data
Jul. 28, 2015   (JP) ................ 2015-148638

(51) Int. Cl.
| | |
|---|---|
| G06F 17/00 | (2006.01) |
| A63B 69/36 | (2006.01) |
| G09B 19/00 | (2006.01) |
| A61B 5/00 | (2006.01) |
| A61B 5/11 | (2006.01) |
| G06F 19/00 | (2018.01) |
| H04M 1/725 | (2006.01) |

(52) U.S. Cl.
CPC .......... *A63B 69/36* (2013.01); *G09B 19/0038* (2013.01); *A61B 5/11* (2013.01); *A61B 5/1122* (2013.01); *A61B 5/6895* (2013.01); *G06F 19/3481* (2013.01); *H04M 1/7253* (2013.01)

(58) Field of Classification Search
None
See application file for complete search history.

(56) References Cited

U.S. PATENT DOCUMENTS

| | | | |
|---|---|---|---|
| 2011/0224012 A1* | 9/2011 | Hashimoto | A63B 69/3632 473/223 |
| 2013/0150121 A1* | 6/2013 | Jeffery | H04W 4/00 455/556.1 |
| 2014/0379293 A1 | 12/2014 | Sato | |
| 2016/0001127 A1 | 1/2016 | Sato | |
| 2017/0028251 A1 | 2/2017 | Ito et al. | |
| 2017/0028254 A1 | 2/2017 | Ito et al. | |
| 2017/0028282 A1 | 2/2017 | Ito et al. | |
| 2017/0028283 A1 | 2/2017 | Ito et al. | |
| 2017/0036082 A1 | 2/2017 | Kodaira et al. | |

FOREIGN PATENT DOCUMENTS

| | | |
|---|---|---|
| JP | 2004-135908 A | 5/2004 |
| JP | 2008-073210 A | 4/2008 |
| JP | 2015-002910 A | 1/2015 |
| JP | 2016-013302 A | 1/2016 |

(Continued)

*Primary Examiner* — Paul A D'Agostino
(74) *Attorney, Agent, or Firm* — Oliff PLC

(57) ABSTRACT

A swing diagnosis apparatus includes a level calculator that calculates a level based on the relationship among at least one imaginary plane, the position of a hitting section of a sport gear at a first timing during a backswing, and the position of the hitting section at a second timing during a downswing.

23 Claims, 19 Drawing Sheets

(56) References Cited

FOREIGN PATENT DOCUMENTS

| | | |
|---|---|---|
| JP | 2017-023637 A | 2/2017 |
| JP | 2017-023638 A | 2/2017 |
| JP | 2017-023639 A | 2/2017 |
| JP | 2017-023640 A | 2/2017 |
| JP | 2017-023643 A | 2/2017 |
| JP | 2017-029460 A | 2/2017 |

* cited by examiner

PHYSICAL INFORMATION

HEIGHT [cm]    170

GENDER    ◉ MALE   ○ FEMALE

AGE    36

COUNTRY    JAPAN

GOLF CLUB INFORMATION

CLUB LENGTH [cm]    115

CLUB NUMBER    1W

FIG. 4

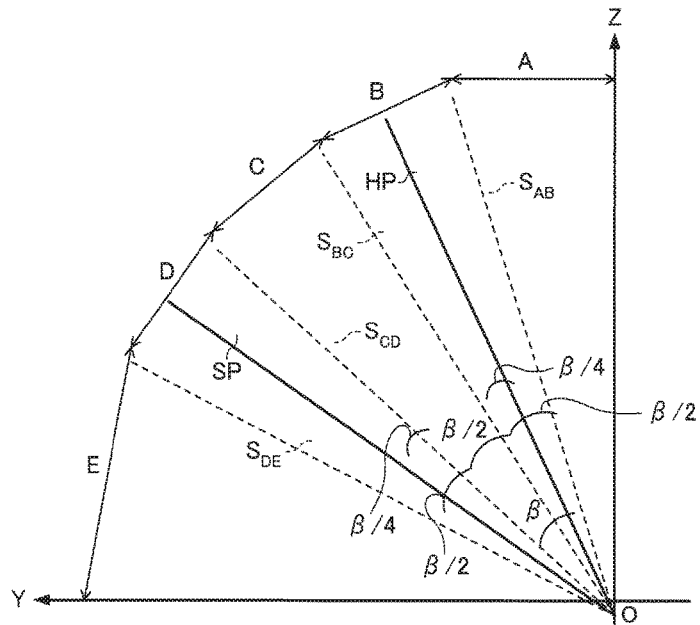

FIG. 15

| V-ZONE SCORE TABLE | | HEAD POSITION IN HALFWAY DOWN STATE | | | | |
|---|---|---|---|---|---|---|
| | | A | B | C | D | E |
| HEAD POSITION IN HALFWAY BACK STATE | A | pv1 | pv2 | pv3 | pv4 | pv5 |
| | B | pv6 | pv7 | pv8 | pv9 | pv10 |
| | C | pv11 | pv12 | pv13 | pv14 | pv15 |
| | D | pv16 | pv17 | pv18 | pv19 | pv20 |
| | E | pv21 | pv22 | pv23 | pv24 | pv25 |

FIG. 16

| SPEED SCORE TABLE | | 1 | 2 | 3 | 4 | 5 |
|---|---|---|---|---|---|---|
| MALE | DRIVER | SMALLER THAN vh1 | vh1~vh2 | vh2~vh3 | vh3~vh4 | GREATER THAN OR EQUAL TO vh4 |
| | IRON | SMALLER THAN vh5 | vh5~vh6 | vh6~vh7 | vh7~vh8 | GREATER THAN OR EQUAL TO vh8 |
| FEMALE | DRIVER | SMALLER THAN vh11 | vh11~vh12 | vh12~vh13 | vh13~vh14 | GREATER THAN OR EQUAL TO vh14 |
| | IRON | SMALLER THAN vh15 | v15~vh16 | vh16~vh17 | vh17~vh18 | GREATER THAN OR EQUAL TO vh18 |

FIG. 17

SWING DIAGNOSIS APPARATUS, SWING DIAGNOSIS SYSTEM, SWING DIAGNOSIS METHOD, AND RECORDING MEDIUM

BACKGROUND

1. Technical Field

The present invention relates to a swing diagnosis apparatus, a swing diagnosis system, a swing diagnosis method, and a recording medium.

2. Related Art

JP-A-2004-135908 describes a measurement system including a sensor device that senses passage of a club head so swung down as to hit a golf ball, an impact camera that captures video images of the club and the golf ball at the impact, a first ball measurement camera and a second ball measurement camera set in positions separate from each other by a predetermined distance along the flight line (flight trajectory) of the hit ball, an apparatus that measures the performance of the golf club, and a monitor that displays the state of the motion of the golf ball. The measurement system analyzes the state of the motion of the hit golf ball on the basis of the video images and displays the state of the motion of the golf ball in a radar chart. The measurement system therefore readily allows assessment of the performance of the golf club on the basis the state of the motion of the golf ball.

The measurement system described in JP-A-2004-135908, however, displays the state of the motion of the hit golf ball, that is, data after the impact in a radar chart, and it is therefore difficult to grasp characteristics of the swing up to the impact even by reviewing the radar chart.

SUMMARY

An advantage of some aspects of the invention is to provide a swing diagnosis apparatus, a swing diagnosis system, a swing diagnosis method, and a recording medium capable of clearly showing characteristics of the swing up to the impact.

The invention can be implemented in the form of the following aspects or application examples:

Application Example 1

A swing diagnosis apparatus according to this application example includes a level calculator that calculates a level based on a relationship among at least one imaginary plane, a position of a hitting section of a sport gear at a first timing during a backswing, and the position of the hitting section at a second timing during a downswing.

The sport gear is a gear used to perform a swing and may, for example, be a golf club, a tennis racket, a baseball bat, and a hockey stick.

The level calculator may calculate the level on the basis of data on the swing. The data on the swing may be, for example, measured data on acceleration or angular velocity of the swing or analysis information containing values of indices representing the characteristics of the swing obtained by analysis of the measured data. Instead, the data on the swing may be data in which part or entirety of the values of the indices representing the characteristics of the swing are pseudo values. Still instead, the data on the swing may be data based on an output signal from an inertial sensor that measures the acceleration or the angular velocity of the swing.

The swing diagnosis apparatus according to this application example can calculate the level on the basis of the relationship between the imaginary plane and the positions of the hitting section of the sport gear at desired timings during the backswing and during the downswing to clearly show the characteristics of the swing up to the impact in the form of the level.

Application Example 2

In the swing diagnosis apparatus according to the application described above, the at least one imaginary plane may include a first imaginary plane identified based on a first axis along a target direction of a hit ball and a second axis along a longitudinal direction of the sport gear before the backswing starts.

The target direction of a hit ball may be a direction in a reference plane (horizontal plane, for example).

The swing diagnosis apparatus according to this application example can clearly show the characteristics of the swing in the form of the level on the basis of the relationship between the first imaginary plane and the positions of the hitting section of the sport gear at desired timings during the backswing and during the downswing.

Application Example 3

In the swing diagnosis apparatus according to the application described above, the at least one imaginary plane may include a second imaginary plane identified based on a first axis along a target direction of a hit ball and a third axis inclined with respect to a longitudinal direction of the sport gear before the backswing starts by a first angle.

The swing diagnosis apparatus according to this application example can clearly show the characteristics of the swing in the form of the level on the basis of the relationship between the second imaginary plane and the positions of the hitting section of the sport gear at desired timings during the backswing and during the downswing.

Application Example 4

In the swing diagnosis apparatus according to the application described above, the level calculator may provide a lower level based on the relationship when an expected hit ball is likely to curve by a greater amount.

The phrase "likely to curve" may mean that the trajectory of the hit ball is likely to curve or that the direction of the hit ball is likely to deviate from the target direction. On the other hand, the level calculator may provide a higher level when the hit ball is likely to fly straighter. The phrase "likely to fly straight" may mean that the trajectory of the hit ball is unlikely to curve or that the direction of the hit ball is unlikely to deviate from the target direction.

The swing diagnosis apparatus according to this application example can clearly show the characteristics of the swing up to the impact in the form of the level in accordance with the degree by which the hit ball is likely to curve.

Application Example 5

In the swing diagnosis apparatus according to the application described above, the first timing may be a point of time when a longitudinal direction of the sport gear coincides with a direction along a horizontal direction during the backswing, and the second timing may be a point of time when the longitudinal direction of the sport gear coincides with the direction along the horizontal direction during the downswing.

The swing diagnosis apparatus according to this application example can calculate the level on the basis of the relationship between the imaginary plane and the positions of the hitting section of the sport gear at the timings when the longitudinal direction of the sport gear during the backswing and during the downswing roughly coincides with the horizontal direction to clearly show the characteristics of the swing in the form of the level based on the difference in the trajectory between the backswing and the downswing.

Application Example 6

In the swing diagnosis apparatus according to the application described above, the level calculator may calculate the level based on a speed of the hitting section at an impact.

The level calculator may calculate the level on the basis of the speed of the hitting section at the impact, in addition to the level calculated on the basis of the relationship described above. Instead, the level calculator may calculate one level (overall score) on the basis of the relationship described above and the speed of the hitting section at the impact.

The swing diagnosis apparatus according to this application example can clearly show the characteristics of the swing in the form of the level on the basis of the speed of the hitting section of the sport gear at the impact.

Application Example 7

In the swing diagnosis apparatus according to the application described above, the level calculator may provide a lower level when the speed is smaller.

On the other hand, the level calculator may provide a higher level when the speed is greater.

The swing diagnosis apparatus according to this application example can clearly show the characteristics of the swing in the form of the level in accordance with the degree of the speed of the hitting section at the impact.

Application Example 8

The swing diagnosis apparatus according to the application described above may further include a display section that displays the level calculated by the level calculator.

The swing diagnosis apparatus according to this application example can present information on the characteristics of the swing up to the impact in the form of the level in a visually understandable manner.

Application Example 9

In the swing diagnosis apparatus according to the application described above, the level may be a score.

The swing diagnosis apparatus according to this application example can clearly show the characteristics of the swing up to the impact in the form of numerals.

Application Example 10

A swing diagnosis system according to this application example includes the swing diagnosis apparatus of any of the application examples described above and an inertial sensor, and the level calculator calculates the level based on an output from the inertial sensor.

The inertial sensor may be a sensor capable of measuring an inertial quantity, such as acceleration and angular velocity, and may, for example, be an inertial measurement unit (IMU) capable of measuring acceleration or angular velocity. Further, for example, the inertial sensor may be attached to a portion of the sport gear or a user and may be detachable from the sport gear or the user or may be built in the sport gear or otherwise fixed to the sport gear so that the inertial sensor cannot be detached.

The swing diagnosis system according to this application example can calculate the level on the basis of an output from the inertial sensor and on the basis of the relationship between the imaginary plane and the positions of the hitting section of the sport gear at desired timings during the backswing and during the downswing to clearly show the characteristics of the swing up to the impact in the form of the level.

Application Example 11

A swing diagnosis method according to this application example includes a procedure of calculating a level based on a relationship among at least one imaginary plane, a position of a hitting section of a sport gear at a first timing during a backswing, and the position of the hitting section at a second timing during a downswing.

Application Example 12

A swing diagnosis program according to this application example causes a computer to perform a procedure of calculating a level based on a relationship among at least one imaginary plane, a position of a hitting section of a sport gear at a first timing during a backswing, and the position of the hitting section at a second timing during a downswing.

Application Example 13

A recording medium according to this application example records a swing diagnosis program that causes a computer to perform a procedure of calculating a level based on a relationship among at least one imaginary plane, a position of a hitting section of a sport gear at a first timing during a backswing, and the position of the hitting section at a second timing during a downswing.

The swing diagnosis method, the swing diagnosis program, and the recording medium according to the application examples described above allow calculation of the level on the basis of the relationship between the imaginary plane and the positions of the hitting section of the sport gear at desired timings during the backswing and during the downswing so that the characteristics of the swing up to the impact is clearly shown in the form of the level.

BRIEF DESCRIPTION OF THE DRAWINGS

The invention will be described with reference to the accompanying drawings, wherein like numbers reference like elements.

FIG. 4 shows an example of an input screen onto which physical information and golf club information are inputted.

FIG. 15 shows an example of the relationship between the shaft plane/the Hogan plane and a plurality of areas.

FIG. 16 shows an example of a V-zone score table.

FIG. 17 shows an example of a speed score table.

DESCRIPTION OF EXEMPLARY EMBODIMENTS

Preferable embodiments of the invention will be described below in detail with reference to the drawings. It is not intended that the embodiments described below unduly limit the contents of the invention set forth in the appended claims. Further, all configurations described below are not necessarily essential configuration requirements of the invention.

The following description will be made with reference to a swing diagnosis system that diagnoses a golf swing.

1. Swing Diagnosis System

1-1. First Embodiment

1-1-1. Configuration of Swing Diagnosis System

Figure 1:
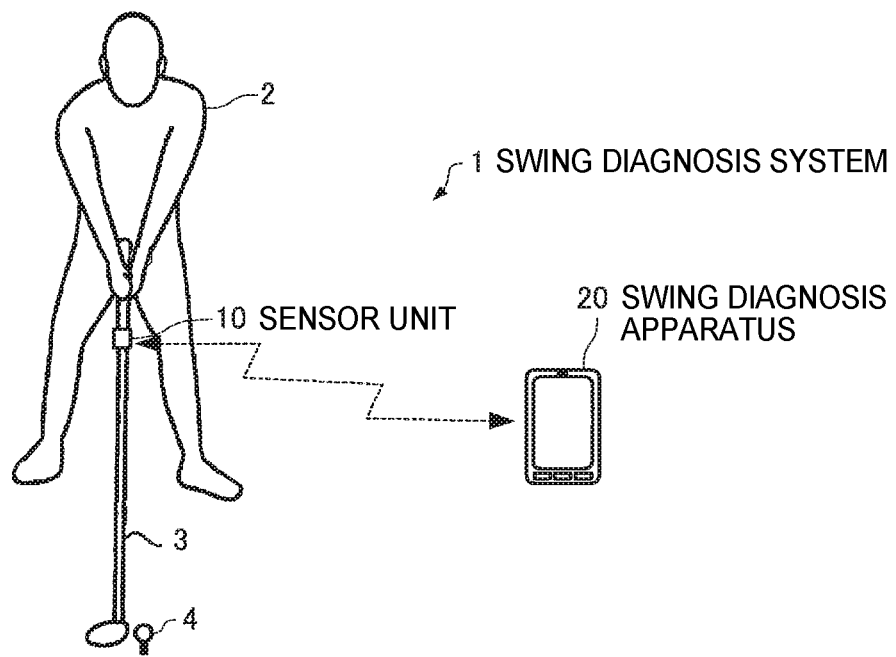
FIG. 1 describes an overview of a swing diagnosis system according to a first embodiment.

FIG. 1 describes an overview of a swing diagnosis system according to a first embodiment. A swing diagnosis system 1 according to the first embodiment includes a swing diagnosis apparatus 20.

A sensor unit 10 (example of inertial sensor) is capable of measuring acceleration produced in each of the three axes and angular velocity produced around each of the three axes, and the sensor unit 10 is attached to a golf club 3.

Figure 2:
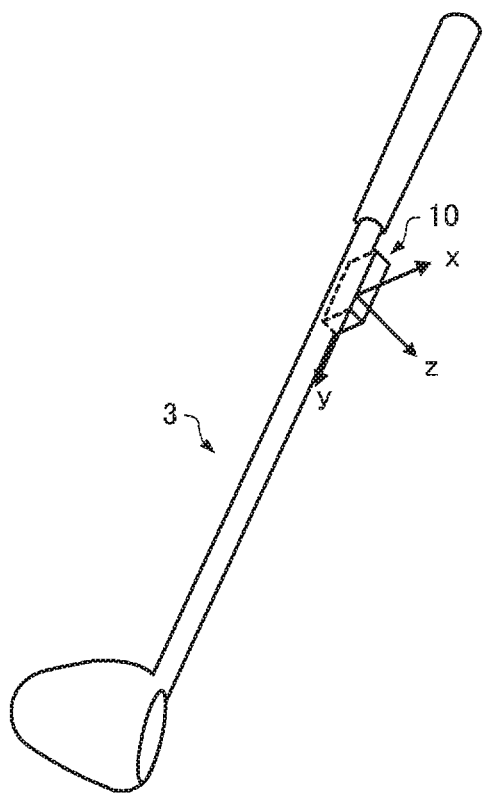
FIG. 2 shows an example of the position where a sensor unit is attached and the direction in which the attached sensor unit is oriented.

In the present embodiment, the sensor unit 10 is attached to part of the shaft of the golf club 3 in such a way that the direction of one of three detection axes (x axis, y axis, and z axis), for example, the y axis, coincides with the longitudinal direction of the shaft (longitudinal direction of golf club 3), as shown in FIG. 2. The sensor unit 10 is desirably attached to a position close to the grip to which the impact produced at the time of ball hitting is unlikely to be transferred and on which centrifugal force is unlikely to act at the time of swing. The shaft is a haft section of the golf club 3 excluding the head but including the grip. It is noted that the sensor unit 10 may instead be attached to a portion of a user 2 (hand, glove, or any other portion, for example) or may still instead be attached to a wristwatch or any other accessory.

Figure 3:
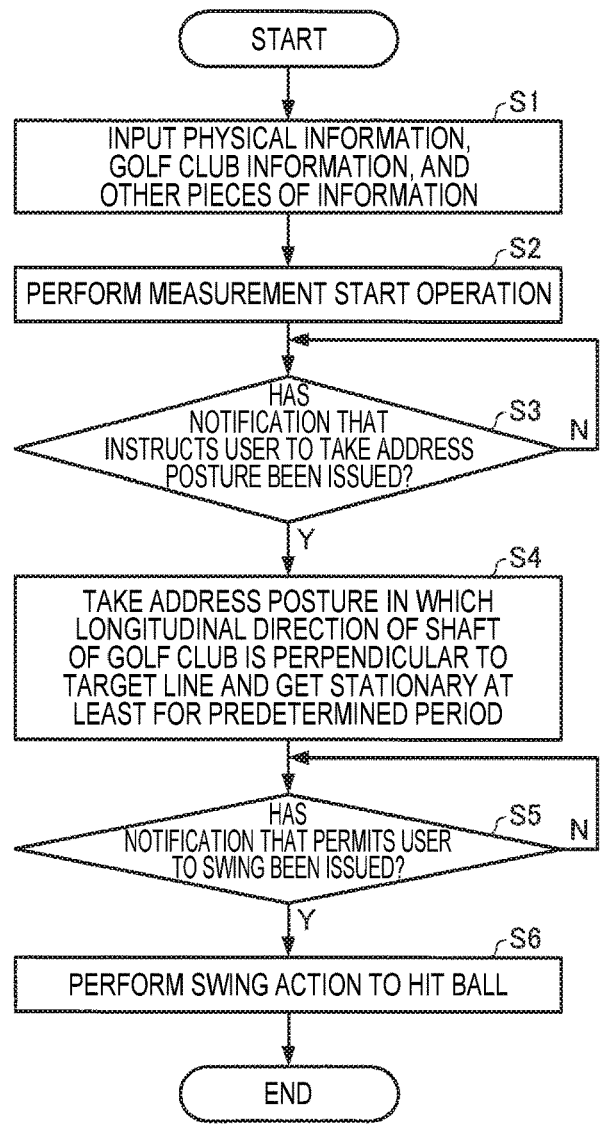
FIG. 3 shows the procedure of actions performed by a user until the user hits a ball.

The user 2 performs a swing action to hit a golf ball 4 in accordance with a predetermined procedure. FIG. 3 shows the procedure of actions performed by the user 2 until the user 2 hits the golf ball 4 in the present embodiment. As shown in FIG. 3, the user 2 first inputs, via the swing diagnosis apparatus 20, physical information on the user 2 and information on the golf club 3 to be used by the user 2 (golf club information) (S1). The physical information includes at least one of the height, the arm length, and the leg length on the user 2 and may further include gender information and other pieces of information. The golf club information includes at least one of the length of the golf club 3 (club length) and the type (club number) of the golf club 3. The user 2 then performs measurement start operation via the swing diagnosis apparatus 20 (operation of causing sensor unit 10 to start measurement) (S2). The user 2 then receives, from the swing diagnosis apparatus 20, notification (notification in the form of voice, for example) that instructs the user 2 to take an address posture (basic posture before starting swing) (Y in S3) and then takes the address posture in which the longitudinal direction of the shaft of the golf club 3 is perpendicular to a target line (target direction of hit ball) and gets stationary (S4). The user 2 then receives, from the swing diagnosis apparatus 20, notification (notification in the form of voice, for example) that permits the user 2 to swing (Y in S5) and then performs a swing action to hit the golf ball 4 (S6).

FIG. 4 shows an example of an input screen which is displayed in a display section 25 (see FIG. 7) of the swing diagnosis apparatus 20 and onto which the physical information and the golf club information are inputted. In step S1 in FIG. 3, the user 2 inputs the physical information, such as the height, gender, age, and country, onto the input screen shown in FIG. 4 and inputs the golf club information, such as the club length (length of shaft) and the club number. The information contained in the physical information is not limited to the information described above and may contain, for example, at least one of the arm length and the leg length in place of or in addition to the height. Similarly, information contained in the golf club information is not limited to the information described above and, for example, may not contain at least one of the club length and the club number or may contain any other piece of information.

When the user 2 performs the measurement start operation in step 2 in FIG. 3, the swing diagnosis apparatus 20 transmits a measurement start command to the sensor unit 10, and the sensor unit 10 receives the measurement start command and starts measurement of the three-axis acceleration and the three-axis angular velocity. The sensor unit 10 measures the three-axis acceleration and the three-axis angular velocity in a predetermined cycle (1 ms, for example) and successively transmits the measured data to the swing diagnosis apparatus 20. The communication between the sensor unit 10 and the swing diagnosis apparatus 20 may be wireless communication or wired communication.

The swing diagnosis apparatus 20 notifies the user 2 of the swing start permission shown in step S5 in FIG. 3 and then analyzes the swing action in which the user 2 used the golf club 3 to hit a ball (step S6 in FIG. 3) on the basis of the measured data from the sensor unit 10 (example of output from inertial sensor).

The swing action performed by the user 2 in step S6 in FIG. 3 contains a swing start (backswing), a halfway back state in which the shaft of the golf club 3 is horizontally oriented during the backswing, a top state in which the backswing is switched to the downswing, a halfway down state in which the shaft of the golf club 3 is horizontally oriented during the downswing, and impact (ball hitting) in which the golf club 3 hits the golf ball 4. The swing diagnosis apparatus 20 then generates swing analysis data containing the time (date and hour) when the swing was performed, identification information on the user 2 and the user's gender, the type of the golf club 3, information on a result of the analysis of the swing action.

The swing diagnosis apparatus 20 uses the swing analysis data generated on the basis of the measured data from the sensor unit 10 to calculate levels of predetermined items representing the characteristics of the swing of the user 2. Specifically, the swing diagnosis apparatus 20 calculates the levels of two items, "a V zone" and "a speed," on a scale of 5, for example. The meanings of the two items and a method for calculating each of the two items will be described later. The swing diagnosis apparatus 20 may further calculate an overall point of the swing on the basis of the levels of the two items. The "level" may be expressed, for example, in the form of "1, 2, 3, . . . ," "A, B, C, . . . ," or "O, X, Δ, . . . ," or in the form of scores.

Figure 6:
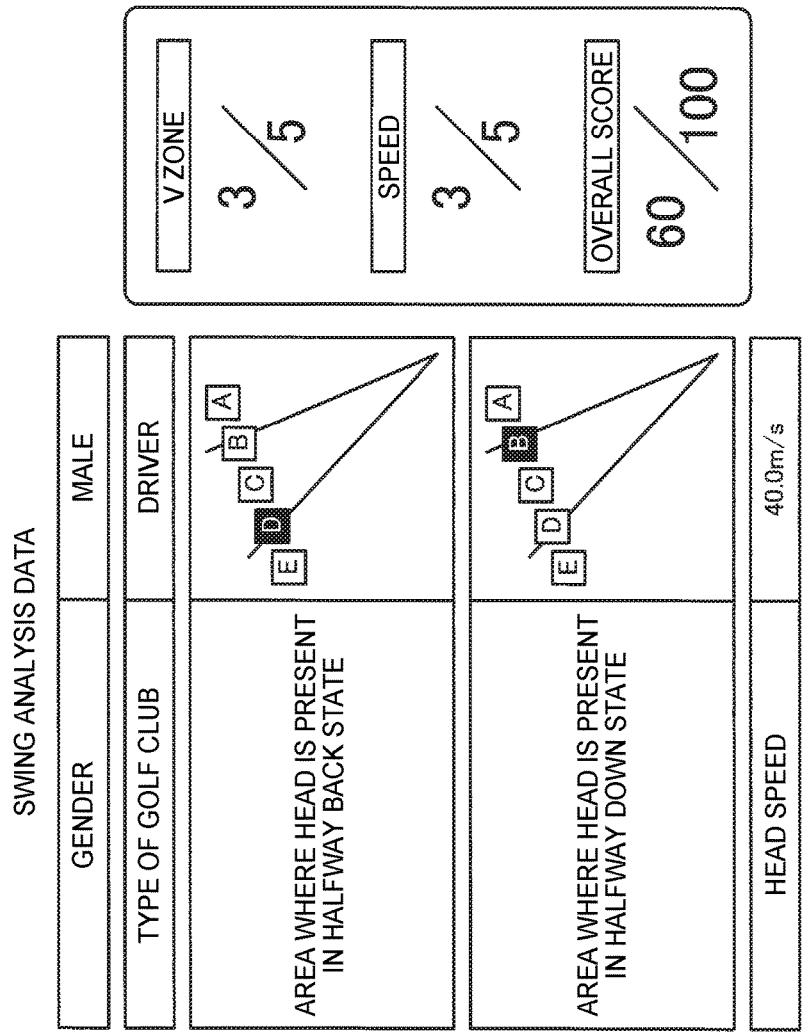
FIG. 6 shows an example of a swing diagnosis screen.

The swing diagnosis apparatus 20 then uses information on the calculated levels of the predetermined items and the calculated overall score to cause the display section 25 to display a swing diagnosis screen shown, for example, in FIG. 6. The swing diagnosis screen shown in FIG. 6 contains information on the swing analysis data on the left. The information on the swing analysis data is information on data used by the swing diagnosis apparatus 20 for the swing diagnosis (calculation of levels of two items and overall score). The information on the swing analysis data contains values associated with the gender, the type of golf club (either driver or iron), and indices of the swing and obtained on the basis of the swing analysis data. The meanings of the indices (area where the head is present in the halfway back state, area where the head is present in the halfway down state, and head speed) and a method for calculating each of the indices will be described later. The swing diagnosis screen shown in FIG. 6 further contains information on scores as the levels of the two items and the overall score on the right.

The user 2 who looks at the swing diagnosis screen shown in FIG. 6 can grasp the levels of the predetermined items and the overall score as a result of diagnosis of the swing analysis data on the left. In particular, the user 2 who looks at the swing diagnosis screen shown in FIG. 6 can grasp a strong point and a weak point of the user's swing. The following description will be made with reference to the case where the "levels" of the predetermined items are expressed by "scores." It is, however, of course, noted that the "levels" can instead be readily expressed, for example, by "1, 2, 3, . . . ," "A, B, C, . . . ," or "O, X, Δ, . . . ."

The swing diagnosis apparatus 20 may be embodied, for example, by using a smartphone, a personal computer, or any information terminal (client terminal).

1-1-2. Configurations of Sensor Unit and Swing Diagnosis Apparatus

Figure 7:
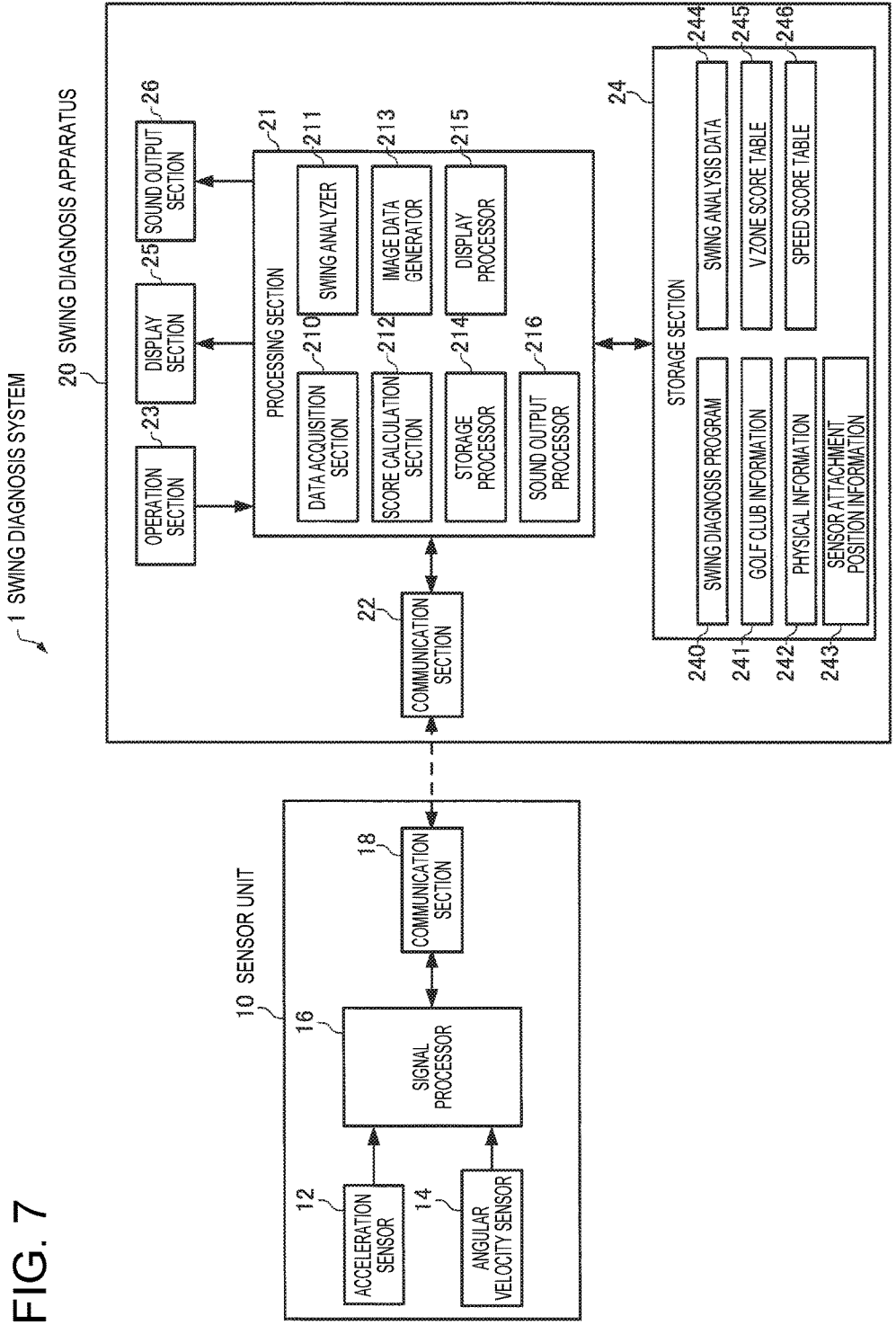
FIG. 7 shows an example of the configuration of the swing diagnosis system according to the first embodiment.

FIG. 7 shows an example of the configuration of the swing diagnosis system 1 (example of configurations of sensor unit 10 and swing diagnosis apparatus 20) according to the first embodiment. In the present embodiment, the sensor unit 10 includes an acceleration sensor 12, an angular velocity sensor 14, a signal processor 16, and a communication section 18, as shown in FIG. 7. It is, however, noted that the sensor unit 10 may have a configuration in which part of the components described above is deleted or changed as appropriate or another component is added as appropriate.

The acceleration sensor 12 measures acceleration produced in three-axis directions perpendicular to each other (ideally at right angles) and outputs a digital signal (acceleration data) according to the magnitudes and orientations of the measured three-axis acceleration.

The angular velocity sensor 14 measures angular velocity produced in the three-axis directions perpendicular to each other (ideally at right angles) and outputs a digital signal (angular velocity data) according to the magnitudes and orientations of the measured three-axis angular velocity.

The signal processor 16 receives the acceleration data and the angular velocity data from the acceleration sensor 12 and the angular velocity sensor 14, adds time information to the two types of data, stores the resultant data in a storage section that is not shown, generates communication-format-complying packet data from the stored measured data (acceleration data and angular velocity data) to which time information has been added, and outputs the packet data to the communication section 18.

The acceleration sensor 12 and the angular velocity sensor 14 are ideally attached to the sensor unit 10 in such a way that the three axes of each of the sensors coincide with the three axes (x axis, y axis, and z axis) of an orthogonal coordinate system (sensor coordinate system) defined with respect to the sensor unit 10, but a practical attachment angle has an error. In view of the fact described above, the signal processor 16 uses a correction parameter calculated in advance in accordance with the error in the attachment angle to convert the acceleration data and the angular velocity data into data in the xyz coordinate system.

The signal processor 16 may further perform temperature correction on the measured data from the acceleration sensor 12 and the angular velocity sensor 14. A temperature correction function may instead be incorporated in each of the acceleration sensor 12 and the angular velocity sensor 14.

Each of the acceleration sensor 12 and the angular velocity sensor 14 may output an analog signal. In this case, the signal processor 16 may A/D-convert an output signal from the acceleration sensor 12 and an output signal from the angular velocity sensor 14 to generate measured data (acceleration data and angular velocity data) and use the measured data to generate packet data for communication.

The communication section 18 transmits the packet data received from the signal processor 16 to the swing diagnosis apparatus 20, receives a variety of control commands, such as the measurement start command, from the swing diagnosis apparatus 20 and transmits the control commands to the signal processor 16, and carries out other processes. The signal processor 16 carries out a variety of processes according to the control commands.

In the present embodiment, the swing diagnosis apparatus 20 includes a processing section 21, a communication section 22, an operation section 23, a storage section 24, the display section 25, and a sound output section 26, as shown in FIG. 7. It is, however, noted that the swing diagnosis apparatus 20 may have a configuration in which part of the components described above is deleted or changed as appropriate or another component is added as appropriate.

The communication section 22 receives the packet data transmitted from the sensor unit 10 and transmits the packet data to the processing section 21, transmits the control commands from the processing section 21 to the sensor unit 10, and carries out other processes.

The operation section 23 acquires data according to operation performed by the user 2 and sends the data to the processing section 21. The operation section 23 may, for example, be a touch-panel-type display, buttons, keys, or a microphone.

The storage section 24 is formed, for example, of a ROM (read only memory), a flash ROM, a RAM (random access memory), or any of a variety of IC memories, a hard disk drive, a memory card, or any other recording medium, or any other components. The storage section 24 stores programs used by the processing section 21 to carry out a variety of calculation processes and control processes, a variety of programs and data for achieving application functions, and other pieces of information.

In the present embodiment, the storage section 24 stores a swing diagnosis program 240 read by the processing section 21 for the swing diagnosis. The swing diagnosis program 240 may be stored in a nonvolatile recording medium (computer readable recording medium) in advance, or the processing section 21 may receive the swing diagnosis program 240 from a server that is not shown over a network and store the received swing diagnosis program 240 in the storage section 24.

Further, in the present embodiment, the storage section 24 stores golf club information 241, physical information 242, sensor attachment position information 243, and swing analysis data 244. For example, the user 2 may operate the operation section 23 to input information on the specifications of the golf club 3 to be used (for example, at least part of information on length of shaft, position of center of gravity, lie angle, face angle, loft angle, and other parameters) onto the input screen in FIG. 4 and set the input specification information to be the golf club information 241. Instead, in step S1 in FIG. 3, the user 2 may input the product number of the golf club 3 (or select product number from product number list) and set information on the specifications corresponding to the inputted product number, among the pieces of information on the specifications stored on a product number basis in advance in the storage section 24, to be the golf club information 241.

Further, for example, the user 2 may operate the operation section 23 to input physical information onto the input screen shown in FIG. 4 to set the inputted physical information to be the physical information 242. Moreover, for example, in step S1 in FIG. 3, the user 2 may operate the operation section 23 to input the distance between the position where the sensor unit 10 is attached and the grip end of the golf club 3 and set the information on the inputted distance to be the sensor attachment position information 243. Instead, assuming that the sensor unit 10 is attached in a predetermined position set in advance (for example, position separate from grip end by 20 cm), the information on the predetermined position may be stored in advance as the sensor attachment position information 243.

The swing analysis data 244 is data containing the time (date and hour) when the swing was performed, identification information on the user 2 and the user's gender, the type of the golf club 3, information on a result of the swing action analysis performed by the processing section 21 (swing analyzer 211).

The storage section 24 further stores a V-zone score table 245 and a speed score table 246. The score tables will be described later in detail.

The storage section 24 is further used as a work area by the processing section 21 and temporarily stores data acquired via the operation section 23, results of computation performed by the processing section 21 in accordance with a variety of programs, and other pieces of information. The storage section 24 may further store data required to be saved for a long period among data generated in the processes carried out by the processing section 21.

The display section 25 displays a result of a process carried out by the processing section 21 in the form of letters, a graph, a table, or an animation or any other image. The display section 25 may, for example, be a CRT, an LCD, a touch-panel-type display, or a head mounted display (HMD). The functions of the operation section 23 and the display section 25 may be achieved by a single touch-panel-type display.

The sound output section 26 outputs a result of a process carried out by the processing section 21 in the form of voice, buzzer sound, or any other type of sound. The sound output section 26 may, for example, be a loudspeaker or a buzzer.

The processing section 21 carries out, in accordance with a variety of programs, the process of transmitting the control commands to the sensor unit 10 via the communication section 22 and a variety of types of calculation processes on the data received from the sensor unit 10 via the communication section 22. The processing section 21 further reads the swing analysis data 244 from the storage section 24, calculates the scores of the predetermined items and the overall score, displays the swing diagnosis screen (FIG. 6), and carries out other processes in accordance with the variety of programs. The processing section 21 still further carries out a variety of other control processes.

In particular, in the present embodiment, the processing section 21 executes the swing diagnosis program 240 to function as a data acquirer 210, a swing analyzer 211, a score calculator 212, an image data generator 213, a storage processor 214, a display processor 215, and a sound output processor 216 and diagnoses the swing action of the user 2 (swing diagnosis). In the present embodiment, the swing diagnosis includes analysis of the swing action of the user 2 (swing analysis) and calculation of the scores of the swing action (score calculation).

The data acquirer 210 receives the packet data received by the communication section 22 from the sensor unit 10, acquires the time information and the measured data from the received packet data, and sends the time information and the measured data to the storage processor 214.

The storage processor 214 reads and writes a variety of programs and a variety of data from and to the storage section 24. For example, the storage processor 214 causes the storage section 24 to store the time information and the measured data received from the data acquirer 210 with the time information and the measured data related to each other and causes the storage section 24 to store a variety of pieces of information calculated by the swing analyzer 211, the swing analysis data 244, and other pieces of information. Further, for example, the storage processor 214 reads the swing analysis data 244, the V-zone score table 245, and the speed score table 246 stored in the storage section 24 and sends them to the score calculator 212.

The swing analyzer 211 uses the measured data outputted by the sensor unit 10 (measured data stored in storage section 24), data from the operation section 23, and other types of data to analyze the swing motion of the user 2 to generate the swing analysis data 244 containing the time (date and hour) when the swing was performed, identification information on the user 2 and the user's gender, the type of the golf club 3, and information on a result of the analysis of the swing action. In particular, in the present embodiment, the swing analyzer 211 calculates values of the indices of the swing as at least part of the information on a result of the analysis of the swing action.

The swing analyzer 211 may calculate at least one imaginary plane as an index of the swing. For example, the at least one imaginary plane includes a shaft plane SP (first imaginary plane) and a Hogan plane HP (second imaginary plane), which is inclined with respect to the shaft plane SP by a first angle, and the swing analyzer 211 may calculate the "shaft plane SP" and the "Hogan plane" as the index.

The swing analyzer 211 may calculate, as an index of the swing, the position of the head of the golf club 3 at a first timing during the backswing. For example, the first timing occurs in the halfway back state, in which the longitudinal direction of the golf club 3 coincides with the horizontal direction during the backswing, and the swing analyzer 211 may calculate "the head position in the halfway back state" as the index.

The swing analyzer 211 may further calculate, as an index of the swing, the position of the head of the golf club 3 at a second timing during the downswing. For example, the second timing occurs in the halfway down state, in which the longitudinal direction of the golf club 3 coincides with the horizontal direction during the downswing, and the swing analyzer 211 may calculate "the head position in the halfway down state" as the index.

The swing analyzer 211 may further calculate, as an index of the swing, an index based on the speed of the golf club 3 at the impact (at the time of ball hitting). For example, the swing analyzer 211 may calculate "a head speed," which will be described later, as the index.

It is, however, noted that the swing analyzer 211 may not calculate values of part of the indices described above as appropriate or may calculate a value of another index as appropriate.

The score calculator 212 (level calculator) calculates the scores (levels) of the predetermined items representing the characteristics of the swing of the user 2 on the basis of data on the swing. In the present embodiment, the data on the swing is the swing analysis data 244.

The score calculator 212 further calculates the overall score on the basis of the scores of the predetermined items. The score calculator 212 then sends information on the calculated scores of the predetermined items and the calculated overall score to the image data generator 213.

The image data generator 213 generates image data corresponding to an image to be displayed in the display section 25. For example, the image data generator 213 generates image data corresponding to the swing diagnosis screen shown in FIG. 6 on the basis of the information on the scores of the predetermined items and the overall score received from the score calculator 212.

The display processor 215 cause the display section 25 to display a variety of images (not only image corresponding to image data generated by image data generator 213 but also letters, symbols, and other objects). For example, the display processor 215 causes the display section 25 to display the swing diagnosis screen shown in FIG. 6 and other objects on the basis of the image data generated by the image data generator 213. Further, for example, the display processor 215 may cause the display section 25 to display an image, letters, or any other object for notifying the user 2 of the swing start permission in step S5 in FIG. 3. Moreover, for example, the display processor 215 may cause the display section 25 to display, after the user 2 completes the swing motion, text information, such as letters and symbols, representing a result of the analysis performed by the swing analyzer 211 automatically or in accordance with input operation performed by the user 2. Instead, the sensor unit 10 may be provided with a display section, and the display processor 215 may transmit image data to the sensor unit 10 via the communication section 22 to cause the display section of the sensor unit 10 to display a variety of images, letters, and other objects.

The sound output processor 216 causes the sound output section 26 to output a variety of types of sound (including voice, buzzer sound, and other types of sound). For example, the sound output processor 216 may cause the sound output section 26 to output sound for notifying the user 2 of the swing start permission in step S5 in FIG. 3. Further, for example, the sound output processor 216 may cause, after the user 2 completes the swing motion, the sound output section 26 to output sound or voice representing a result of the analysis performed by the swing analyzer 211 automatically or in accordance with input operation performed by the user 2. Instead, the sensor unit 10 may be provided with a sound output section, and the sound output processor 216 may transmit a variety of sound data or voice data to the sensor unit 10 via the communication section 22 to cause the sound output section of the sensor unit 10 to output the variety of types of sound or voice.

The swing diagnosis apparatus 20 or the sensor unit 10 may be provided with a vibration mechanism, and the vibration mechanism may convert a variety of pieces of information into vibration information and notify the user 2 of the vibration information.

1-1-3. Swing Analysis

Figure 5:
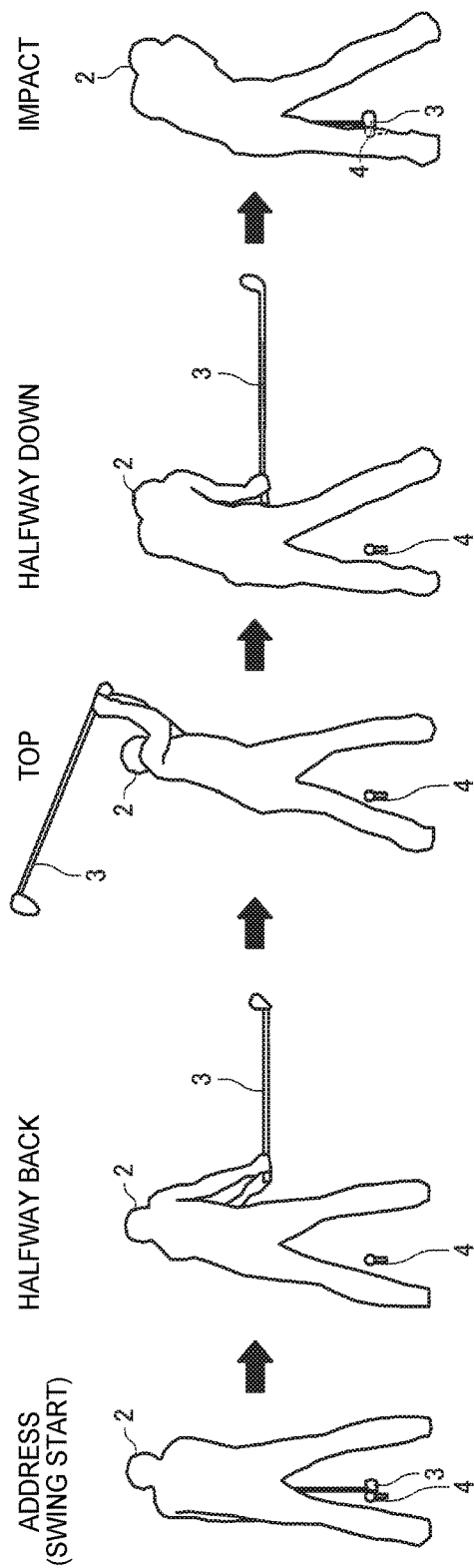
FIG. 5 describes a swing action.

In the present embodiment, an XYZ coordinate system (global coordinate system) is defined as follows: The position of the head of the golf club 3 in an address posture (stationary state) is the origin; the target line representing the target direction along which the ball is hit is the X axis; an axis perpendicular to the X axis and present in the horizontal plane is the Y axis; and the vertically upward direction (direction opposite direction of gravitational acceleration) is the Z axis. To calculate the index values, the swing analyzer 211 then uses the measured data from the sensor unit 10 (acceleration data and angular velocity data) to calculate the position and posture of the sensor unit 10 in the XYZ coordinate system (global coordinate system) over time from the time when the user takes the address posture. The swing analyzer 211 further uses the measured data from the sensor unit 10 (acceleration data and angular velocity data) to detect the timings of the swing start, the top state, and the impact shown in FIG. 5. The swing analyzer 211 then uses the time-course data on the position and posture of the sensor unit 10 and the timings of the swing start, the top state, and the impact to calculate the indices of the swing (for example, shaft plane, Hogan plane, head position in halfway back state, head position in halfway down state, and head speed) and generates the swing analysis data 244.

Calculation of Position and Posture of Sensor Unit 10

When the user 2 performs the action in step S4 in FIG. 3, and the amount of change in the acceleration data measured with the acceleration sensor 12 keeps being smaller than or equal to a threshold for a predetermined period, the swing analyzer 211 first determines that the user 2 takes an address posture and gets stationary. The swing analyzer 211 then uses the measured data (acceleration data and angular velocity data) within the predetermined period to calculate the amount of offset contained in the measured data. The swing analyzer 211 then subtracts the amount of offset from the measured data for bias correction and uses the bias-corrected measured data to calculate the position and posture of the sensor unit 10 during the swing action of the user 2 (during action in step S6 in FIG. 3).

Specifically, the swing analyzer 211 first uses the acceleration data measured with the acceleration sensor 12, the golf club information 241, and the sensor attachment position information 243 to calculate the position of the sensor unit 10 in the XYZ coordinate system (global coordinate system) at the time when the user 2 is stationary (takes address posture) (initial position).

Figure 8:
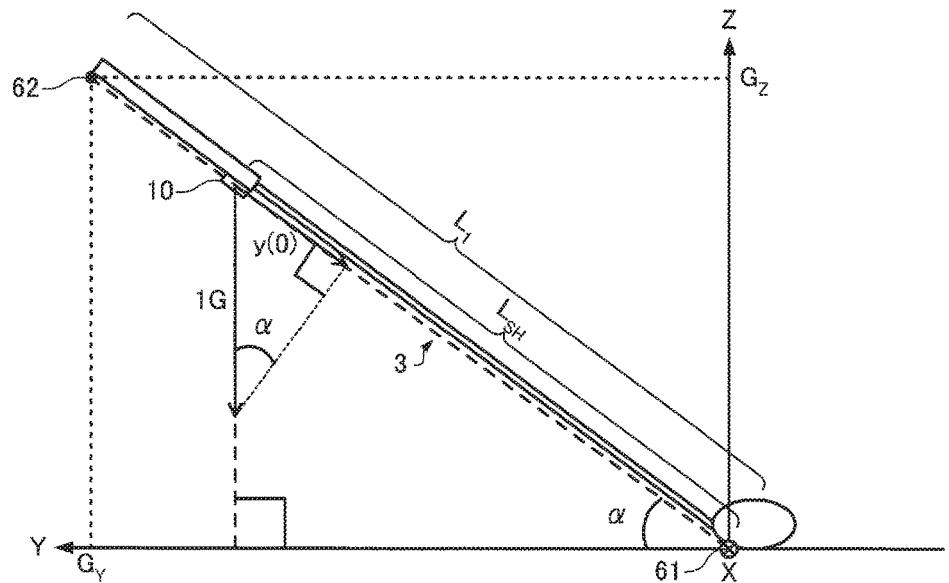
FIG. 8 is a plan view of a golf club and the sensor unit viewed from the negative side of an X axis at the time when the user is stationary.

FIG. 8 is a plan view of the golf club 3 and the sensor unit 10 viewed from the negative side of the X axis at the time when the user 2 is stationary (takes address posture). A position 61 of the head of the golf club 3 coincides with the origin O (0, 0, 0), and the coordinates of a position 62 of the grip end are (0, $G_Y$, $G_Z$). Since the user 2 performs the action in step S4 in FIG. 3, the position 62 of the grip end and the initial position of the sensor unit 10 have an X coordinate of 0 and are present in the YZ plane. Since gravitational acceleration 1 G acts on the sensor unit 10 when the user 2 is stationary, the relationship between y-axis acceleration y(0) measured with the sensor unit 10 and an inclination angle α of the shaft of the golf club 3 (angle between longitudinal direction of shaft and horizontal plane (XY plane)) is expressed by Expression (1).

$$y(0) = 1G \cdot \sin \alpha \quad (1)$$

The swing analyzer 211 can therefore calculate the inclination angle α by substituting arbitrary acceleration data between arbitrary points of time at the time when the user takes the address posture (is stationary) into Expression (1).

The swing analyzer 211 then subtracts a distance $L_{SG}$, which is the distance between the sensor unit 10 and the grip end and contained in the sensor attachment position information 243, from a length $L_1$, which is the length of the shaft and contained in the golf club information 241, to determine a distance $L_{SH}$, which is the distance between the sensor unit 10 and the head. The swing analyzer 211 further sets the initial position of the sensor unit 10 to be the position separate from the head position 61 (origin O) by the distance $L_{SH}$ in the direction identified by the inclination angle α of the shaft (negative direction of y axis of sensor unit 10).

The swing analyzer 211 then integrates the following acceleration data to calculate a time-course set of the coordinates of the position of the sensor unit 10 starting from the initial position thereof.

The swing analyzer 211 further uses the acceleration data measured with the acceleration sensor 12 to calculate the posture of the sensor unit 10 in the XYZ coordinate system (global coordinate system) at the time when the user is stationary (takes address posture) (initial posture). Since the user 2 performs the action in step S4 in FIG. 3, the direction of the x axis of the sensor unit 10 coincides with the direction of the X axis of the XYZ coordinate system when the user 2 takes the address posture (is stationary), and the y axis of the sensor unit 10 is present in the YZ plane, whereby the swing analyzer 211 can identify the initial posture of the sensor unit 10 from the inclination angle α of the shaft of the golf club 3.

The swing analyzer 211 then performs rotation operation using the angular velocity data measured with the angular velocity sensor 14 after the initial posture to calculate time-course changes in the posture of the sensor unit 10 starting from the initial posture. The posture of the sensor unit 10 can be expressed, for example, by angles of rotation around the X axis, the Y axis, and the Z axis (roll angle, pitch angle, and yaw angle) or quaternions.

It is noted that the signal processor 16 of the sensor unit 10 may calculate the amount of offset in the measured data and perform the bias correction on the measured data, or the bias correction function may be incorporated in the acceleration sensor 12 and the angular velocity sensor 14. In these cases, the swing analyzer 211 does not need to perform the bias correction on the measured data.

Detection of Timings of Swing Start, Top State, and Impact

The swing analyzer 211 first uses the measured data to detect the timing when the user 2 has hit the ball (impact timing). For example, the swing analyzer 211 may calculate a combined value of the measured data (acceleration data or angular velocity data) and detect the impact timing (point of time) on the basis of the combined value.

Specifically, for example, the swing analyzer 211 first uses the angular velocity data (bias-corrected angular velocity data at each point of time t) to calculate a combined value $n_0$ (t) of the angular velocity at each point of time t. For example, let x(t), y(t), and z(t) be the angular velocity data at a point of time t, and the swing analyzer 211 calculates the combined value $n_0$ (t) of the angular velocity by using the following Expression (2).

$$n_0(t) = \sqrt{x(t)^2 + y(t)^2 + z(t)^2} \quad (2)$$

The swing analyzer 211 then converts the combined value $n_0$ (t) of the angular velocity at each point of time t into a combined value n(t) normalized (scale-converted) over a predetermined range. For example, let max ($n_0$) be the maximum of the combined value of the angular velocity in a measured data acquisition period, and the swing analyzer 211 converts the combined value $n_0$ (t) of the angular velocity into a combined value n(t) normalized over the range from 0 to 100 by using the following Expression (3).

$$n(t) = \frac{100 \times n_0(t)}{\max(n_0)} \quad (3)$$

The swing analyzer 211 then calculates derivative dn(t) of the normalized combined value n(t) at each point of time t. For example, let Δt be the cycle of the three-axis angular velocity data measurement, and the swing analyzer 211 calculates the derivative (difference) dn(t) of the combined value of the angular velocity at point of time t by using the following Expression (4).

$$dn(t)=n(t)-n(t-\Delta t) \quad (4)$$

Figure 9:
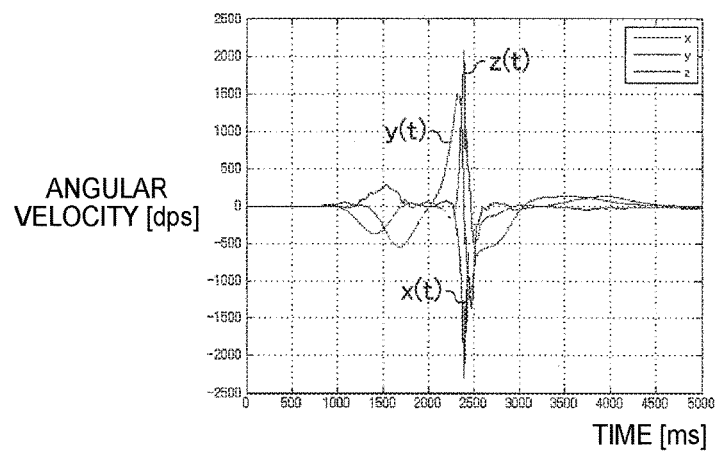
FIG. 9 shows graphs illustrating temporal changes in three-axis angular velocity.

FIG. 9 shows an example of the three-axis angular velocity data x(t), y(t), and z(t) obtained when the user 2 performs swing action to hit the golf ball 4. In FIG. 9, the horizontal axis represents time (msec), and the vertical axis represents the angular velocity (dps).

Figure 10:
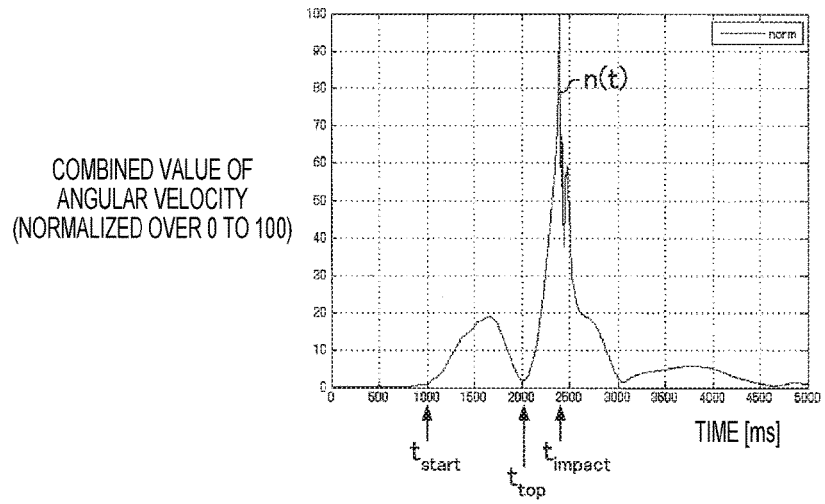
FIG. 10 shows a graph illustrating temporal changes in a combined value of the three-axis angular velocity.

FIG. 10 shows a graph illustrating the combined value n(t) obtained by normalization of the combined value $n_0$ (t) of the three-axis angular velocity, which is calculated from the three-axis angular velocity data x(t), y(t), and z(t) in FIG. 9 in accordance with Expression (2), over the range from 0 to 100 in accordance with Expression (3). In FIG. 10, the horizontal axis represents time (msec), and the vertical axis represents the combined value of the angular velocity.

Figure 11:
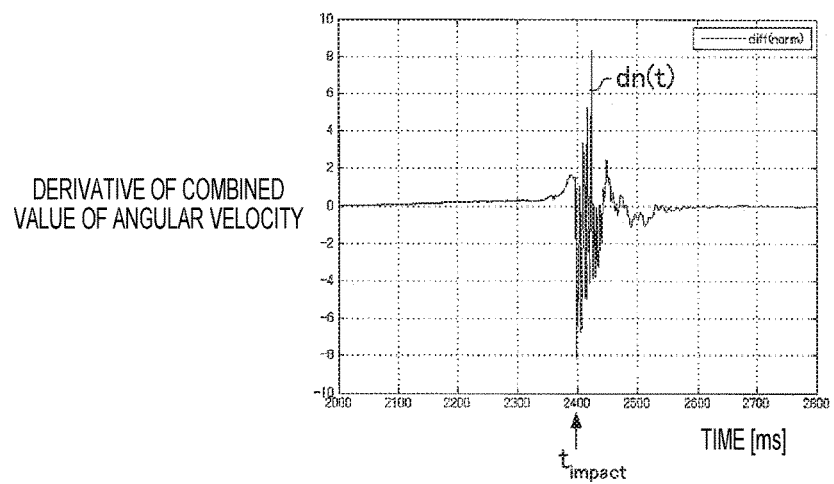
FIG. 11 shows a graph illustrating temporal changes in the derivative of the combined value.

FIG. 11 shows a graph illustrating the derivative dn(t) calculated from the combined value n(t) of the three-axis angular velocity in FIG. 10 in accordance with Expression (4). In FIG. 11, the horizontal axis represents time (msec), and the vertical axis represents the derivative of the combined value of the three-axis angular velocity. It is noted that the horizontal axis ranges from 0 to 5 seconds in FIGS. 9 and 10 but the horizontal axis ranges from 2 to 2.8 seconds in FIG. 11 so that changes in the derivative before and after the impact are legible.

The swing analyzer 211 then selects the point of time when the derivative dn(t) of the combined value is maximized and the point of time when the derivative dn(t) of the combined value is minimized and detects the earlier one of the two points of time as impact time $t_{impact}$ (impact timing) (see FIG. 11). In a typical golf swing, it is believed that the swing speed is maximized at the moment of impact. Further, since it is believed that the combined value of the angular velocity changes in accordance with the swing speed, the swing analyzer 211 can capture, as the impact timing, the timing when the derivative of the combined value of the angular velocity is maximized or minimized (that is, timing when the derivative of the combined value of the angular velocity is positive maximum or negative minimum) in the series of moments of the swing action. Since the golf club 3 vibrates due to the impact, the timing when the derivative of the combined value of the angular velocity is maximized and the timing when the derivative of the combined value of the angular velocity is minimized are believed to occur as a pair, and the earlier timing is believed to be the moment of impact.

The swing analyzer 211 then detects, as a point of time $t_{top}$ of the top state (top timing), the time of a local minimum which is before the point of time of the impact $t_{impact}$ and when the combined value n(t) approaches zero (see FIG. 10). In a typical golf swing, it is believed that after the swing starts, the swing action temporarily stops in the top state, and the swing speed then gradually increases until the impact. The swing analyzer 211 can therefore capture, as the top timing, the timing which is before the impact timing and when the combined value of the angular velocity approaches zero and becomes locally minimized.

Now, let top segments be the segments which are before and after the point of time $t_{top}$ of the top state and where the combined value n(t) is smaller than or equal to a predetermined threshold, and the swing analyzer 211 then detects, as a point of time $t_{start}$ when the swing starts (backswing starts), the latest point of time when the combined value n(t) becomes smaller than or equal to the predetermined threshold before the time when the top segments start (see FIG. 10). In a typical golf swing, in which the swing action starts from a stationary state, it is difficult to imagine that the swing action stops before the top state. The swing analyzer 211 can therefore capture, as the timing when the swing action starts, the latest timing when the combined value of the angular velocity becomes smaller than or equal to the predetermined threshold before the top segments. The swing analyzer 211 may instead detect, as the point of time $t_{start}$ of swing start, the point of time of a local minimum which is before the point of time $t_{top}$ of the top state and where the combined value n(t) approaches zero.

The swing analyzer 211 can instead use the three-axis acceleration data to similarly detect the timings of the swing start, the top state, and the impact.

Calculation of Shaft Plane and Hogan Plane

The shaft plane is a first imaginary plane identified by the target line (target direction of hit ball) and the longitudinal direction of the shaft of the golf club 3 at the time when the user 2 takes an address posture (is stationary) before the user 2 starts swinging. The Hogan plane is a second imaginary plane identified by an imaginary line that connects a portion in the vicinity of the shoulder of the user 2 (such as shoulder or base of neck) to the head of the golf club (or golf ball 4) and the target line (target direction of hit ball) at the time when the user 2 takes the address posture.

Figure 12:
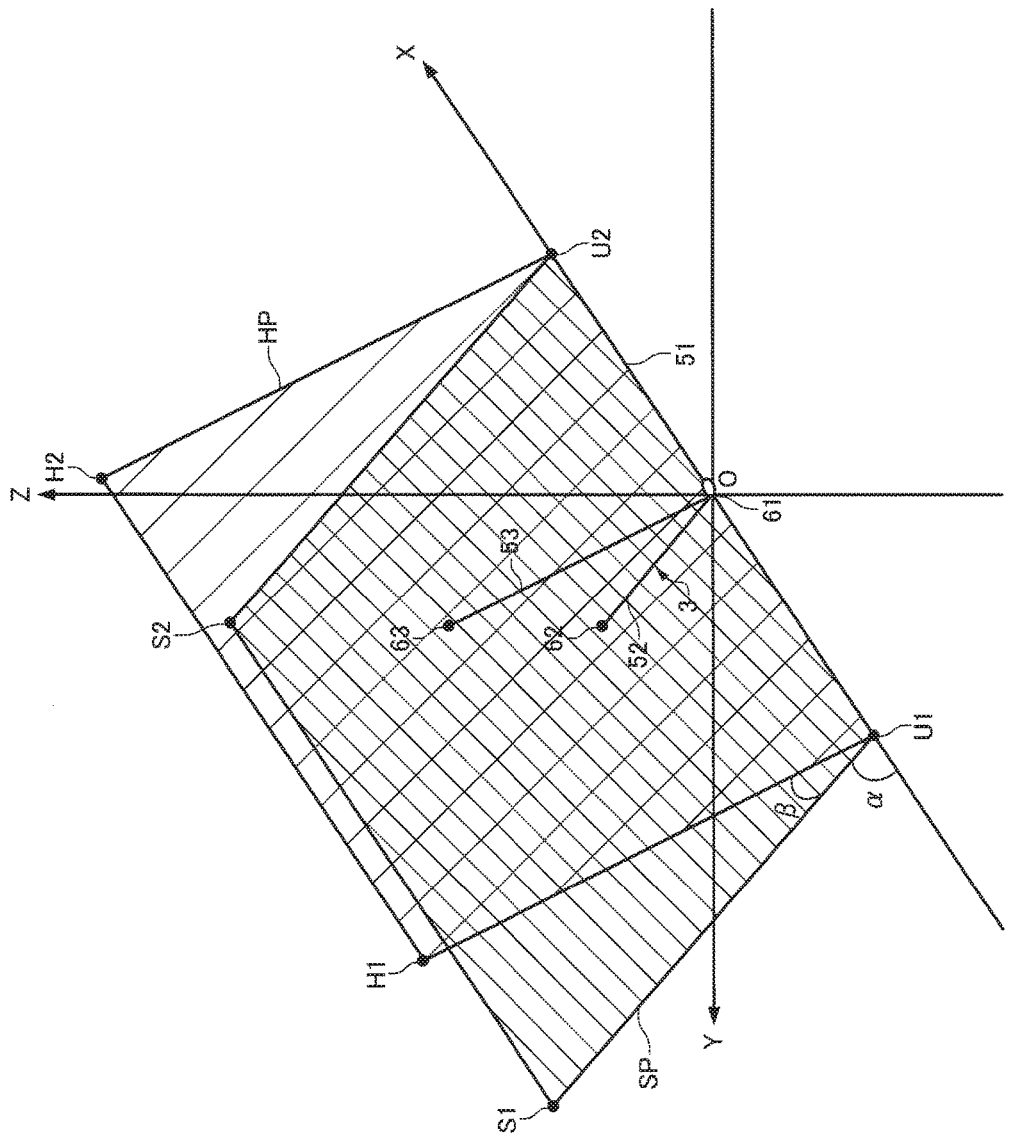
FIG. 12 shows a shaft plane and a Hogan plane.

FIG. 12 shows the shaft plane and the Hogan plane. In FIG. 12, the X axis, the Y axis, and the Z axis of the XYZ coordinate system (global coordinate system) are also drawn.

In the present embodiment, it is assumed that the shaft plane SP (first imaginary plane) is an imaginary plane containing a first line segment 51, which is a first axis along the target direction of the hit ball, and a second line segment 52, which is a second axis along the longitudinal direction of the shaft of the golf club 3, and having four vertices U1, U2, S1, and S2, as shown in FIG. 12. In the present embodiment, it is assumed that the position 61 of the head of the golf club 3 at the time when the user takes an address posture is the origin O (0, 0, 0) of the XYZ coordinate system, and that the second line segment 52 is a line segment that connects the position 61 of the head of the golf club 3 (origin O) to the position 62 of the grip end. Further, the first line segment 51 is a line segment having opposite ends that coincide with U1 and U2 on the X axis, having a middle point that coincides with the origin O, and having a length UL. When the user 2 performs the action in step S4 in FIG. 3 at the time when the user 2 takes an address posture, the shaft of golf club 3 becomes perpendicular to the target line (X axis), and the first line segment 51 is therefore a line segment perpendicular to the longitudinal direction of the shaft of the golf club 3, that is, a line segment perpendicular to the second line segment 52. The swing analyzer 211 calculates the coordinates of the four vertices U1, U2, S1, and S2, which belong to the shaft plane SP, in the XYZ coordinate system.

Specifically, the swing analyzer 211 first uses the inclination angle α and the length $L_1$ of the shaft, which is contained in the golf club information 241, to calculate the coordinates (0, $G_Y$, $G_Z$) of the position 62 of the grip end of the golf club 3. The swing analyzer 211 can use the shaft length $L_1$ and the inclination angle α to calculate $G_Y$ and $G_Z$ by substituting the length $L_1$ of the shaft and the inclination angle α into Expressions (5) and (6), respectively, as shown in FIG. 8.

$$G_Y = L_1 \cdot \cos \alpha \qquad (5)$$

$$G_Z = L_1 \cdot \sin \alpha \qquad (6)$$

The swing analyzer 211 then multiplies the coordinates $(0, G_Y, G_Z)$ of the position 62 of the grip end of the golf club 3 by a scale factor S to calculate the coordinates $(0, S_Y, S_Z)$ of a middle point S3 between the vertex S1 and the vertex S2 in the shaft plane SP. That is, the swing analyzer 211 calculates $S_Y$ and $S_Z$ by using Expressions (7) and (8), respectively.

$$S_Y = G_Y \cdot S \qquad (7)$$

$$S_Z = G_Z \cdot S \qquad (8)$$

Figure 13:
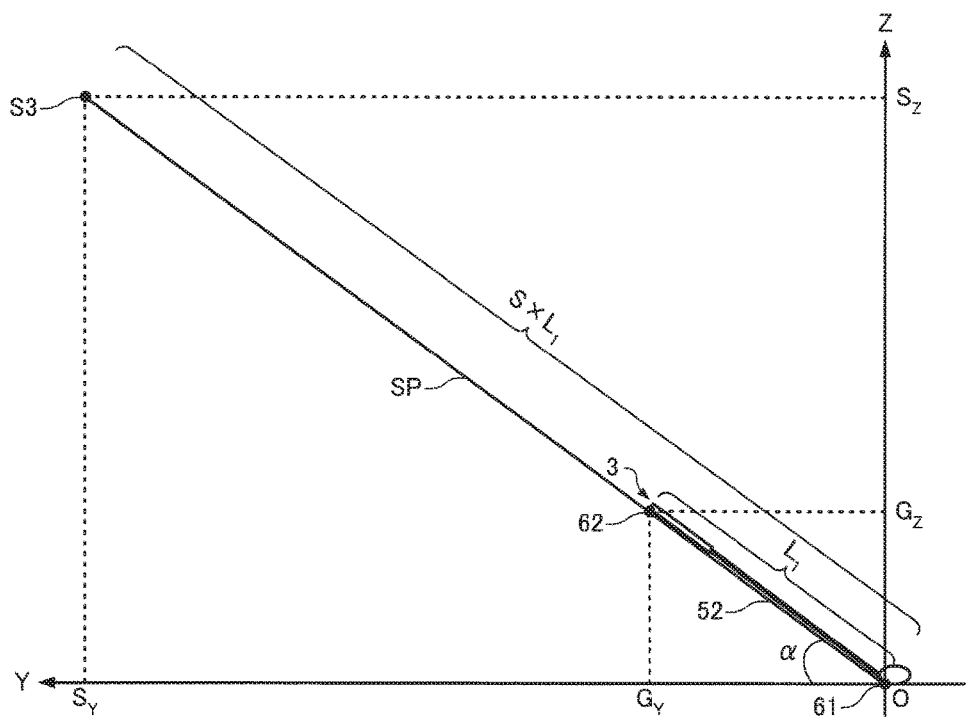
FIG. 13 is a cross-sectional view of the shaft plane taken along a YZ plane and viewed from the negative side of the X axis.

FIG. 13 is a cross-sectional view of the shaft plane SP in FIG. 12 taken along the YZ plane and viewed from the negative side of the X axis. The length of the line segment that connects the middle point S3 between the vertex S1 and the vertex S2 to the origin O (width of shaft plane SP in direction perpendicular to X axis) is the length $L_1$ of the second line segment 52 multiplied by S, as shown in FIG. 13. The value of the scale factor S is so set that the trajectory of the golf club 3 during the swing action of the user 2 falls within the shaft plane SP. For example, let $L_2$ be the length of the arm of the user 2, and the scale factor S may be so set that the width $S \times L_1$ of the shaft plane SP in the direction perpendicular to the X axis is twice the sum of the shaft length $L_1$ and the arm length $L_2$ as expressed by Expression (9).

$$S = \frac{2 \cdot (L_1 + L_2)}{L_1} \qquad (9)$$

The length $L_2$ of the arm of the user 2 correlates with the height $L_0$ of the user 2 and is expressed by a correlation equation, such as Expression (10) in a case where the user 2 is male and Expression (11) in a case where the user 2 is female, on the basis of statistical information.

$$L_2 = 0.41 \times L_0 - 45.5 \text{ [mm]} \qquad (10)$$

$$L_2 = 0.46 \times L_0 - 126.9 \text{ [mm]} \qquad (11)$$

The swing analyzer 211 can therefore use the height $L_0$ of the user 2 and the gender thereof contained in the physical information 242 to calculate the user's arm length $L_2$ by using Expression (10) or (11).

The swing analyzer 211 then uses the coordinates $(0, S_Y, S_Z)$ of the middle point S3 and the width UL of the shaft plane SP in the X-axis direction (length of first line segment 51) to calculate the coordinates $(-UL/2, 0, 0)$ of the vertex U1, the coordinates $(UL/2, 0, 0)$ of the vertex U2, the coordinates $(-UL/2, S_Y, S_Z)$ of the vertex S1, and the coordinates $(UL/2, S_Y, S_Z)$ of the vertex S2 of the shaft plane SP. The value of the width UL in the X-axis direction is so set that the trajectory of the golf club 3 during the swing action of the user 2 falls within the shaft plane SP. For example, the width UL in the X-axis direction may be so set as to be equal to the width $S \times L_1$ in the direction perpendicular to the X axis, that is, twice the sum of the shaft length $L_1$ and the arm length $L_2$.

The swing analyzer 211 can thus calculate the coordinates of the four vertices U1, U2, S1 and S2 of the shaft plane SP.

Further, in the present embodiment, the Hogan plane HP (second imaginary plane) is an imaginary plane containing the first line segment 51 as the first axis and a third line segment 53 as a third axis and having four vertices U1, U2, H1 and H2, as shown in FIG. 12. The third line segment 53 is a line segment that connects a predetermined position 63, which is located in the vicinity of the line segment connecting opposite shoulders of the user 2 to each other, to the position 61 of the head of the golf club 3. The third line segment 53 may instead be the line segment that connects the predetermined position 63 to the position of the golf ball 4. The swing analyzer 211 calculates the coordinates of the four vertices U1, U2, H1 and H2, which belong to the Hogan plane HP, in the XYZ coordinate system.

Specifically, the swing analyzer 211 first uses the coordinates $(0, G_Y, G_Z)$ of the position 62 of the grip end of the golf club 3 at the time when the user takes an address posture (is stationary) and the length $L_2$ of the arm of the user 2 based on the physical information 242 to estimate the predetermined position 63 and calculate the coordinates $(A_X, A_Y, A_Z)$ thereof.

Figure 14:
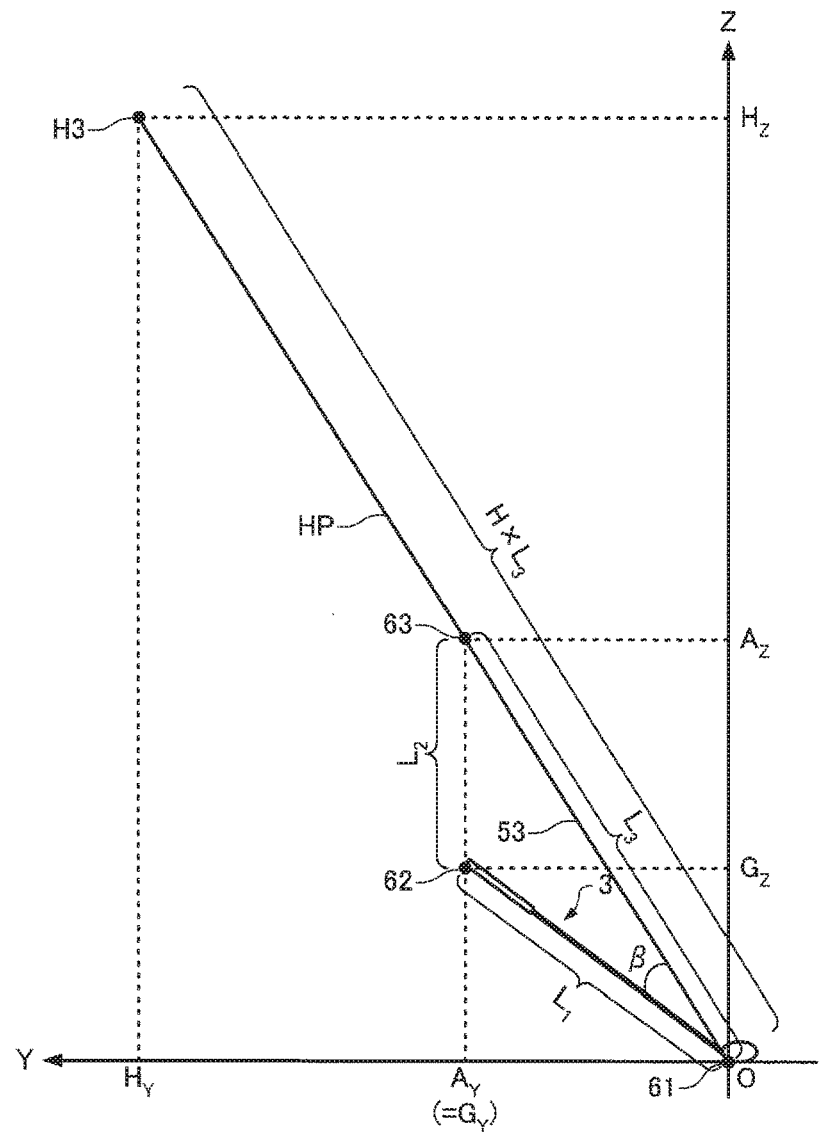
FIG. 14 is a cross-sectional view of the Hogan plane taken along the YZ plane and viewed from the negative side of the X axis.

FIG. 14 is a cross-sectional view of the Hogan plane HP in FIG. 12 taken along the YZ plane and viewed from the negative side of the X axis. In FIG. 14, the predetermined position 63 is the middle point of the line segment connecting opposite shoulders of the user 2 to each other, and the predetermined position 63 is therefore present in the YZ plane. The X coordinate $A_X$ of the predetermined position 63 is therefore zero. The swing analyzer 211 then estimates that the predetermined position 63 is the position shifted from the position 62 of the grip end of the golf club 3 in the positive direction of the Z axis by the length $L_2$ of the arm of the user 2, as shown in FIG. 14. The swing analyzer 211 therefore sets the Y coordinate $A_Y$ of the predetermined position 63 to be equal to the Y coordinate $G_Y$ of the position 62 of the grip end. The swing analyzer 211 further calculates the Z coordinate $A_Z$ of the predetermined position 63 to be equal to the sum of the Z coordinate $G_Z$ of the position 62 of the grip end and the length $L_2$ of the arm of the user 2, as expressed by Expression (12).

$$A_Z = G_Z + L_2 \qquad (12)$$

The swing analyzer 211 then multiplies each of the Y coordinate $A_Y$ and the Z coordinate $A_Z$ of the predetermined position 63 by a scale factor H to calculate the coordinates $(0, H_Y, H_Z)$ of a middle point H3 between the vertex H1 and the vertex H2 in the Hogan plane HP. That is, the swing analyzer 211 calculates $H_Y$ and $H_Z$ by using Expressions (13) and (14), respectively.

$$H_Y = A_Y \cdot H \qquad (13)$$

$$H_Z = A_Z \cdot H \qquad (14)$$

The length of the line segment that connects the middle point H3 between the vertex H1 and the vertex H2 to the origin O (width of Hogan plane HP in direction perpendicular to X axis) is H times the length $L_3$ of the third line segment 53, as shown in FIG. 14. The value of the scale factor H is so set that the trajectory of the golf club 3 during the swing action of the user 2 falls within the Hogan plane HP. For example, the Hogan plane HP may have the same shape and size as those of the shaft plane SP. In this case, the width $H \times L_3$ of the Hogan plane HP in the direction perpendicular to the X axis coincides with the width $S \times L_1$ of the shaft plane SP in the direction perpendicular to the X axis and is twice the sum of the length $L_1$ of the shaft of the golf club 3 and the length $L_2$ of the arm of the user 2. The swing analyzer 211 can therefore calculate the scale factor H by using Expression (15).

$$H = \frac{2 \cdot (L_1 + L_2)}{L_3} \qquad (15)$$

Further, the swing analyzer 211 can use the Y coordinate $A_Y$ and the Z coordinate $A_Z$ of the predetermined position 63 to calculate the length $L_3$ of the third line segment 53 along with Expression (13).

The processing section 21 then uses the coordinates (0, $H_Y$, $H_Z$) of the middle point H3 and the width UL of the Hogan plane HP in the X-axis direction (length of first line segment 51) to calculate the coordinates (−UL/2, $H_Y$, $H_Z$) of the vertex H1 and the coordinates (UL/2, $H_Y$, $H_Z$) of the vertex H2 of the Hogan plane HP. Since the two vertices U1 and U2 of the Hogan plane HP coincide with those of the shaft plane SP, the swing analyzer 211 does not need to calculate the coordinates of the vertices U1 and U2 of the Hogan plane HP over again.

The swing analyzer 211 can thus calculate the coordinates of the four vertices U1, U2, H1, and H2 of the Hogan plane HP.

The area sandwiched between the shaft plane SP (first imaginary plane) and the Hogan plane HP (second imaginary plane) is called a "V zone," and the trajectory of a hit ball (course of hit ball) can be estimated to some extent on the basis of the relationship of the positions of the head of the golf club 3 during the backswing and the downswing with the V zone. For example, when the head of the golf club 3 is present in the space below the V zone at a predetermined timing during the backswing or the downswing, the hit ball tends to hook. On the other hand, when the head of the golf club 3 is present in the space above the V zone at a predetermined timing during the backswing or the downswing, the hit ball tends to slice. In the present embodiment, the first angle β between the shaft plane SP and the Hogan plane HP is determined in accordance with the length $L_1$ of the shaft of the golf club 3 and the length $L_2$ of the arm of the user 2, as clearly shown in FIG. 14. That is, since the first angle β is not a fixed value but is determined in accordance with the type of the golf club 3 and the body of the user 2, a shaft plane SP and a Hogan plane HP (V zone) that are more appropriate as the indices for the diagnosis of the swing of the user 2 are calculated.

Calculation of Head Positions in Halfway Back and Halfway Down States

The head position in the halfway back state is the head position at the instant of, immediately before, or immediately after the halfway back state, and the head position in the halfway down state is the head position at the instant of, immediately before, or immediately after the halfway down state.

The swing analyzer 211 first uses the position and posture of the sensor unit 10 at each point of time t from the point of time $t_{start}$ of the swing start to the point of time $t_{impact}$ of the impact to calculate the head position and the grip end position at each point of time t.

Specifically, the swing analyzer 211 sets the head position to be the position separate from the position of the sensor unit 10 by the distance $L_{SH}$ in the positive direction of the y axis, which is identified by the posture of the sensor unit 10, and calculates the coordinates of the head position. The distance $L_{SH}$ is the distance between the sensor unit 10 and the head, as described above. The swing analyzer 211 further sets the grip end position to be the position separate from the position of the sensor unit 10 by the distance $L_{SG}$ in the negative direction of the y axis, which is identified by the posture of the sensor unit 10, and calculates the coordinates of the grip end position. The distance $L_{SG}$ is the distance between the sensor unit 10 and the grip end, as described above.

The swing analyzer 211 then uses the coordinates of the head position and the coordinates of the grip end position to detect the timing of the halfway back state and the timing of the halfway down state.

Specifically, the swing analyzer 211 calculates a difference ΔZ between the Z coordinate of the head position and the Z coordinate of the grip end position at each point of time t from the point of time $t_{start}$ of the swing start to the point of time $t_{impact}$ of the impact. The swing analyzer 211 then detects, as the halfway back timing, a point of time $t_{HWB}$ which falls within the period from the point of time $t_{start}$ of the swing start to the point of time $t_{top}$ of the top state and when the sign of ΔZ reverses. The swing analyzer 211 further detects, as the halfway down timing, a point of time $t_{HWB}$ which falls within the period from the point of time $t_{top}$ of the top state to the point of time $t_{impact}$ of the impact and when the sign of ΔZ reverses.

The swing analyzer 211 then sets the head position at the point of time $t_{HWB}$ to be the head position in the halfway back state and sets the head position at the point of time $t_{HWD}$ to be the head position in the halfway down state.

Calculation of Head Speed

The head speed is the magnitude of the speed of the head at the impact (instant of impact, immediately before impact, or immediately after impact). For example, the swing analyzer 211 calculates the speed of the head at the point of time $t_{impact}$ of the impact from the difference between the coordinates of the head position at the point of time $t_{impact}$ of the impact and the coordinates of the head position at the preceding point of time. The swing analyzer 211 then calculates the magnitude of the speed of the head as the head speed.

1-1-4. Score Calculation

In the present embodiment, the processing section 21 of the swing diagnosis apparatus 20 (score calculator 212, in particular) performs score calculation in which the scores of the predetermined items, which represent the characteristics of the swing, and the overall score are calculated.

The predetermined items, the scores of which are calculated by the score calculator 212, include an item representing the relationship among at least one of the imaginary planes, the position of the head (example of hitting section) of the golf club 3 (example of sport gear) at the first timing during the backswing, and the position of the head at the second timing during the downswing. For example, the first timing may be a point of time when the longitudinal direction of the golf club 3 coincides with the horizontal direction during the backswing. Further, for example, the second timing may be a point of time when the longitudinal direction of the golf club 3 coincides with the horizontal direction during the downswing.

The at least one imaginary plane may include the shaft plane SP, which is the first imaginary plane identified on the basis of the first line segment 51, which is the first axis along the target direction (target line) of the hit ball in the XY plane as a reference plane, and the second line segment 52, which is the second axis along the longitudinal direction of the golf club 3 at a point of time before the backswing starts. The point of time before the backswing starts may be the point of time of address (point of time when user 2 takes address posture and gets stationary).

The at least one imaginary plane may further include the Hogan plane HP, which is the second imaginary plane (that is, second imaginary plane inclined with respect to first imaginary plane by first angle $\beta$) identified on the basis of the first line segment 51, which is the first axis along the target direction (target line) of the hit ball in the XY plane as a reference plane, and the third line segment 53, which is the third axis inclined with respect to the longitudinal direction of the golf club 3 by the first angle $\beta$ before the backswing starts.

The at least one imaginary plane may include only one of the shaft plane SP and the Hogan plane HP. Instead, the at least one imaginary plane may include another imaginary plane in place of the shaft plane SP and the Hogan plane HP (for example, a flat plane between the shaft plane SP and the Hogan plane HP, a flat plane outside the shaft plane SP and the Hogan plane HP, and a flat plane that intersects at least one of the shaft plane SP and the Hogan plane HP).

In the following description, it is assumed that the predetermined items include an item representing the relationship among "the shaft plane SP," "the Hogan plane HP," "the head position in the halfway back state," and "the head position in the halfway down state," which are the four indices of the swing, (hereinafter the name of the item is referred to as "the V zone").

The predetermined items may further include an item relating to the speed of the golf club 3 at the impact (at the time when the ball is hit). In the following description, it is assumed that the predetermined items include an item representing the relationship among "the head speed," which is an index based on the speed of the golf club 3 at the impact, "the gender," and "the type of the golf club 3," (hereinafter the name of the item is referred to as "the speed").

A method for calculating the scores of the items and a method for calculating the overall score carried out by the score calculator 212 of the processing section 21 will be described in detail.

Calculation of Score of Item "V Zone"

The score calculator 212 calculates the score of the item "V zone" in accordance with which of a plurality of areas determined on the basis of the shaft plane SP and the Hogan plane HP (V zone) the head position in each of the halfway back state and the halfway down state belongs to.

FIG. 15 shows an example of the relationship between the shaft plane SP/the Hogan plane HP (V zone) and the plurality of areas. FIG. 15 shows the relationship among the shaft plane SP, the Hogan plane HP, and five areas A to E viewed from the negative side of the X axis (projected on YZ plane). The area B is a predetermined space containing the Hogan plane HP, and the area D is a predetermined space containing the shaft plane SP. The area C is the space sandwiched between the area B and the area D (space between boundary plane $S_{BC}$ between area B and area C and boundary plane $S_{CD}$ between area C and area D). The area A is the space in contact with the area B, specifically, the boundary plane $S_{AB}$ facing away from the area C. The area E is the space in contact with the area D, specifically, the boundary plane $S_{DE}$ facing away from the area C.

A variety of methods for setting the boundary planes $S_{AB}$, $S_{BC}$, $S_{CD}$, and $S_{DE}$ are conceivable. As an example, the boundary planes can be set as follows: In the YZ plane, the Hogan plane HP is located at the center of the space between the boundary plane $S_{AB}$ and the boundary plane $S_{BC}$; the shaft plane SP is located at the center of the space between the boundary plane $S_{CD}$ and the boundary plane $S_{DE}$; and the angles of the area B, the area C, and the area D around the origin O (X axis) are equal to one another. That is, with respect to the first angle $\beta$ between the shaft plane SP and the Hogan plane HP, when the angles between the Hogan plane HP and the boundary plane $S_{AB}$/the boundary plane $S_{BC}$ are each set at $\beta/4$, and the angles between the shaft plane SP and the boundary plane $S_{CD}$/the boundary plane $S_{DE}$ are each set at $\beta/4$, the angles of the area B, the area C, and the area D are all set at $\beta/2$.

Since no swing in which the head positions in each of the halfway back state and the halfway down state has a negative Y coordinate is conceivable, the boundary plane of the area A opposite the boundary plane $S_{AB}$ is set in the XZ plane. Similarly, since no swing in which the head position in each of the halfway back state and the halfway down state has a negative Z coordinate is conceivable, the boundary plane of the area E opposite the boundary plane $S_{DE}$ is set in the XY plane. It is, of course, noted that the boundary planes of the areas A and E may be so set that the angles of the areas A and E around the origin O (X axis) are equal to the angles of the areas B, C, and D around the origin O.

Specifically, the score calculator 212 first sets the boundary planes $S_{AB}$, $S_{BC}$, $S_{CD}$, and $S_{DE}$ of the areas A to E on the basis of the coordinates of the four vertices U1, U2, S1, and S2 of the shaft plane SP and the coordinates of the four vertices U1, U2, H1, and H2 of the Hogan plane HP contained in the data on the swing (selected swing analysis data 244). The score calculator 212 then determines which of the areas A to E the coordinates of the head position in the halfway back state and the coordinates of the head position in the halfway down state contained in the data on the swing (selected swing analysis data 244) belong to. The score calculator 212 then uses a result of the determination of the area to which the head position in the halfway back state belongs and the area to which the head position in the halfway down state belongs to refer to the V-zone score table 245 and calculates the score corresponding to the result of the determination.

In the present embodiment, the V-zone score table 245 specifies scores corresponding to combinations of an area to which the head position in the halfway back state belongs and an area to which the head position in the halfway down state belongs, as shown in FIG. 16. For example, the score in a case where the head position in the halfway back state belongs to the area A and the head position in the halfway down state belongs to the area A is pv1. Each of the scores pv1 to pv25 shown in FIG. 16 ranges, for example, from 1 to 5.

The score calculator 212 may provide a lower score when the hit ball expected on the basis of the shaft plane SP, the Hogan plane HP, the head position in the halfway back state, and the head position in the halfway down state is likely to curve by a greater amount. The phrase "likely to curve" may mean that the trajectory of the hit ball is likely to curve (likely to slice or hook) or that the direction of the hit ball is likely to deviate from the target direction (target line). On the other hand, the score calculator 212 may provide a higher score when the hit ball is likely to fly straighter. The phrase "likely to fly straight" may mean that the trajectory of the hit ball is unlikely to curve (likely to follow straight line) or that the direction of the hit ball is unlikely to deviate from the target direction (target line).

For example, in a case where the head position in the halfway back state belongs to the area E and the head position in the halfway down state belongs to the area A, it is expected that the hit ball is likely to curve, and the score calculator 212 therefore provides a relatively low score. Therefore, in the example shown in FIG. 16, pv21 may, for example, be 1, which is the lowest score of 1 to 5.

Further, for example, in a case where the head position in the halfway back state and the head position in the halfway down state both belong to the area C, it is expected that the hit ball is likely to fly straight, and the score calculator 212 therefore provides a relatively high score (highest score of 5, for example). Therefore, in the example shown in FIG. 16, pv13 may, for example, be 5, which is the highest score of 1 to 5.

Calculation of Score of Item "Speed"

The score calculator 212 calculates the score of the item "speed" in accordance with which one of a plurality of ranges the head speed belongs to. It is, however, noted that there is a gender difference in the head speed and men typically tends to achieve greater head speeds than women. Further, the head speed differs between the driver and an iron, and the driver typically tends to achieve a greater head speed than irons. It is therefore preferable to select one of the plurality of range settings, in accordance with which the head speed is classified, in accordance with the gender and the type of the golf club to be used. Specifically, the score calculator 212 first determines whether the user 2 is a male or a female and whether the golf club 3 having used is the driver or an iron on the basis of the information on the gender of the user 2 and the information on the type of the golf club 3, which are contained in data on the swing (such as selected swing analysis data 244). The score calculator 212 then selects one of the plurality of range settings, in accordance with which the head speed is classified, on the basis of a result of the determination. The score calculator 212 then determinates which one of the plurality of ranges the head speed contained in the swing analysis data 244 belongs to. The score calculator 212 then refers to the speed score table 246 and calculates the score corresponding to a result of the determination. The score calculator 212 may lower the calculated score as the head speed lowers.

In the present embodiment, the speed score table 246 specifies a plurality of ranges set in accordance with the gender, "male" or "female", and the type of the golf club to be used, "driver" or "iron," and further specifies, for each of the plurality of range settings, a score corresponding to the range to which the head speed belongs to. In the example shown in FIG. 17, in a case of "male" and "driver," the range to which the head speed belongs to is divided into five ranges, "smaller than vh1," "greater than or equal to vh1 but smaller than vh2," "greater than or equal to vh2 but smaller than vh3," "greater than or equal to vh3 but smaller than vh4," and "greater than or equal to vh4." In a case of "male" and "iron," the range to which the head speed belongs to is divided into five ranges, "smaller than vh5," "greater than or equal to vh5 but smaller than vh6," "greater than or equal to vh6 but smaller than vh7," "greater than or equal to vh7 but smaller than vh8," and "greater than or equal to vh8." In a case of "female" and "driver," the range to which the head speed belongs to is divided into five ranges, "smaller than vh11," "greater than or equal to vh11 but smaller than vh12," "greater than or equal to vh12 but smaller than vh13," "greater than or equal to vh13 but smaller than vh14," and "greater than or equal to vh14." In a case of "female" and "iron," the range to which the head speed belongs to is divided into five ranges, "smaller than vh15," "greater than or equal to vh15 but smaller than vh16," "greater than or equal to vh16 but smaller than vh17," "greater than or equal to vh17 but smaller than vh18," and "greater than or equal to vh18." In the settings described above, for example, in the case of "male" and "driver," the score in the case where the head speed belongs to "smaller than vh1" is 1, which is the lowest score of 1 to 5, and the score in the case where the head speed belongs to "greater than or equal to vh4" is 5, which is the highest score of 1 to 5. Further, for example, in the case of "female" and "iron," the score in the case where the head speed belongs to "smaller than vh15" is 1, which is the lowest score of 1 to 5, and the score in the case where the head speed belongs to "greater than or equal to vh18" is 5, which is the highest score of 1 to 5.

Calculation of Overall Score

The score calculator 212 calculates the overall score on the basis of the score of the item "V zone" and the score of the item "speed."

For example, when the score of each of the items is expressed on a scale of 5 and the overall score is expressed on a scale of 100, the score calculator 212 may multiply the score of each of the items by 10 so that the highest score of each of the items is 50 and add the multiplied scores to each other to calculate the overall score. The score of each of the items displayed in the swing diagnosis screen shown in FIG. 6 is expressed on the scale of 5, and the score of each of the items is multiplied by 10 and the multiplied scores are summed to form the overall score of 60.

Further, for example, the score calculator 212 may apply a large weight to an item particularly important in the swing diagnosis (assessment) and sum the scores of the items to calculate the overall score.

1-1-5. Procedure of Swing Diagnosis

Figure 18:
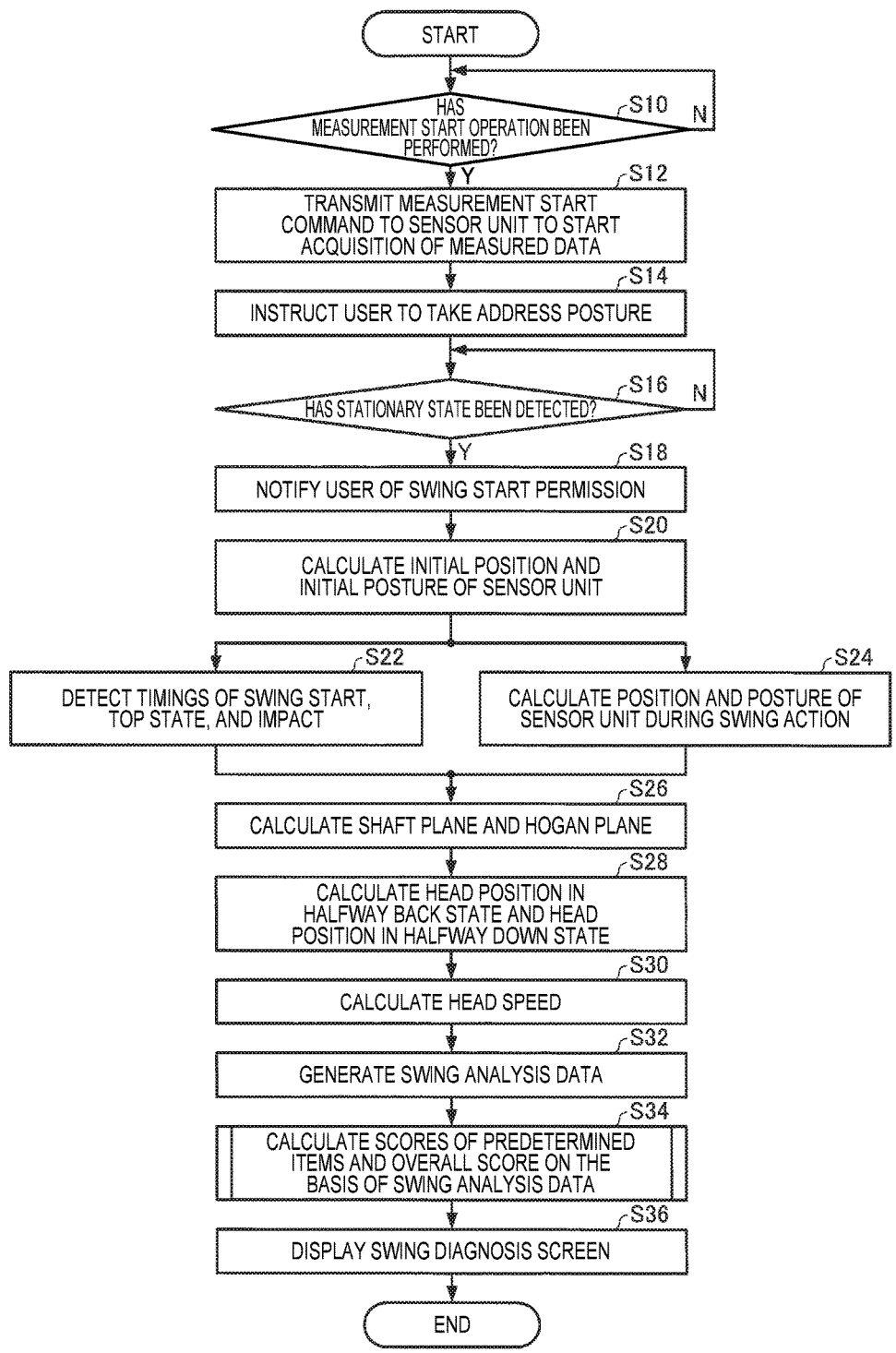
FIG. 18 is a flowchart showing an example of the procedure of swing diagnosis (swing diagnosis method) according to the first embodiment.

FIG. 18 is a flowchart showing an example of the procedure of the swing diagnosis (swing diagnosis method) performed by the processing section 21. The processing section 21 (example of computer) executes the swing diagnosis program 240 stored in the storage section 24 to perform the swing diagnosis, for example, in accordance with the procedure of the flowchart of FIG. 18. The flowchart of FIG. 18 will be described below.

The processing section 21 first waits until the user 2 performs the measurement start operation (operation in step S2 in FIG. 3) (N in step 10) and, when the user 2 performs the measurement start operation (Y in step S10), transmits the measurement start command to the sensor unit 10 to start acquisition of measured data from the sensor unit 10 (S12).

The processing section 21 then instructs the user 2 to take an address posture (S14). The user 2 follows the instruction and takes an address posture and gets stationary (step S4 in FIG. 3).

The processing section 21 then uses the measured data acquired from the sensor unit 10 to detect the stationary state of the user 2 (Y in S16) and notifies the user 2 of swing start permission (S18). The processing section 21 notifies the user 2 of the swing start permission, for example, by outputting predetermined sound, turning on an LED provided in the sensor unit 10, or otherwise issuing notification, and the user 2 starts swing action (action in step S6 in FIG. 3) after the user 2 recognizes the notification.

After the user 2 completes the swing action, or before the user 2 completes the swing action, the processing section 21 carries out the processes in step S20 and the following steps.

The processing section 21 first uses the measured data acquired from the sensor unit 10 (measured data at the time when the user 2 is stationary (takes address posture)) to calculate the initial position and initial posture of the sensor unit 10 (S20).

The processing section 21 then uses the measured data acquired from the sensor unit 10 to detect the timings of the swing start, the top state, and the impact (S22).

The processing section 21 calculates the position and posture of the sensor unit 10 during the swing action of the user 2 (S24) concurrently with, before, or after the process in step S22.

The processing section 21 then proceeds to steps S26 to S30, where the processing section 21 uses at least part of the measured data acquired from the sensor unit 10, the timings of the swing start, the top state, and the impact detected in step S22, and the position and posture of the sensor unit 10 calculated in step S24 to calculate the values of the variety of above-mentioned indices on the swing.

In step S26, the processing section 21 calculates the shaft plane SP and the Hogan plane HP.

In step S28, the processing section 21 calculates the head position in the halfway back state and the head position in the halfway down state.

In step S30, the processing section 21 calculates the head speed.

The processing section 21 then uses the variety of indices calculated in steps S26 to S30 to generate the swing analysis data 244 (S32).

The processing section 21 then calculates the scores of the predetermined items and the overall score (S34) on the basis of the swing analysis data generated in step S32.

The processing section 21 then uses the scores of the predetermined items and the overall score calculated in step S34 to cause the display section 25 to display the swing diagnosis screen (FIG. 6) (S36) and terminates the swing diagnosis.

In the flowchart of FIG. 18, the order of the steps may be changed as appropriate to the extent possible, part of the steps may be deleted or changed, or another step may be added.

Figure 19:
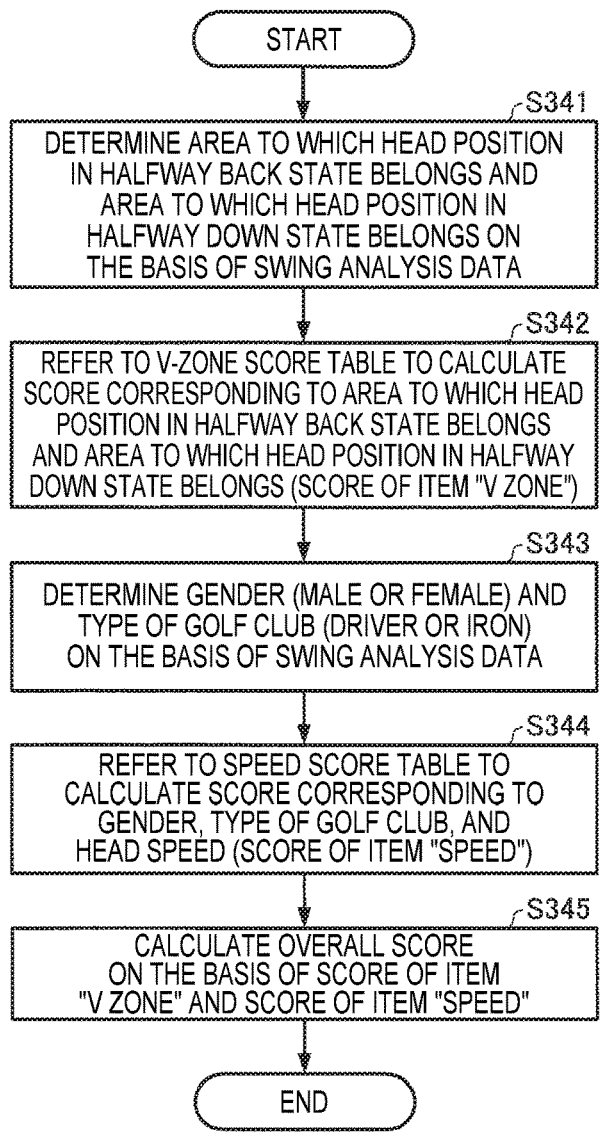
FIG. 19 is a flowchart showing an example of the procedure of the process of calculating scores of predetermined items and an overall score.

FIG. 19 is a flowchart showing an example of the procedure of the process in which the processing section 21 (score calculator 212) calculates the scores of the predetermined items and the overall score (step S34 in FIG. 18). The flowchart of FIG. 19 will be described below.

The processing section 21 first determines the area to which the head position in the halfway back state belongs and the area to which the head position in the halfway down state belongs on the basis of the swing analysis data 244 (S341).

The processing section 21 then refers to the V-zone score table 245 stored in the storage section 24 to calculate the score corresponding to the area to which the head position in the halfway back state belongs and the area to which the head position in the halfway down state belongs (scores in item "V zone") (S342).

The processing section 21 then determines the gender (male or female) and the type of the golf club (driver or iron) on the basis of the swing analysis data 244 (S343).

The processing section 21 then refers to the speed score table 246 stored in the storage section 24 to calculate the score corresponding to the gender, the type of the golf club, and the head speed (score of item "speed") (S344).

Lastly, the processing section 21 calculates the overall score on the basis of the score of the item "V zone" calculated in step S342 and the score of the item "speed" calculated in step S344 (S345).

1-1-6. Advantageous Effects

As described above, according to the swing diagnosis system 1 of the first embodiment, the swing diagnosis apparatus 20 can calculate scores on the basis of the swing analysis data 244 generated by using measured data from the sensor unit 10 and on the basis of the relationship between the imaginary planes and the positions of the head of the golf club 3 at desired timings during the backswing and during the downswing and display the scores in the display section 25 for clear visual recognition of the characteristics of the swing up to the impact in the form of numerals (levels).

In particular, according to the swing diagnosis system 1 of the first embodiment, the swing diagnosis apparatus 20 can use the score of the item "V zone" to clearly show the characteristics of the swing in the form of numerals on the basis of the relationship among the shaft plane SP (first imaginary plane), the Hogan plane HP (second imaginary plane), and the positions of the head of the golf club 3 at desired timings during the backswing and during the downswing (in halfway back state and halfway down state). For example, the swing diagnosis apparatus 20 can provide a lower score of the item "V zone" when the hit ball is likely to curve by a greater amount to clearly show the characteristics of the swing up to the impact in the form of numerals in accordance with the degree by which the hit ball is likely to curve.

Further, according to the swing diagnosis system 1 of the first embodiment, the swing diagnosis apparatus 20 can use the score of the item "speed" to clearly show the characteristics of the swing in the form of numerals on the basis of the speed of the head of the golf club 3 at the impact. For example, the swing diagnosis apparatus 20 can provide a lower score of the item "speed" when the speed of the head is lower to clearly show the characteristics of the swing in the form of numerals in accordance with the degree of the speed of the head at the impact.

The user 2 can therefore grasp the level of the swing, a strong point and a weak point of the swing, a problem with the swing, and other pieces of information from the score of the item "V zone" and the score of the item "speed" obtained as a result of the diagnosis based on the swing analysis data 244.

Further, according to the swing diagnosis system 1 of the first embodiment, since the sensor unit 10 is used to perform the swing analysis and the swing diagnosis, use of a camera or any other massive apparatus is not required, whereby restriction on the place where the user 2 performs a swing decreases.

1-2. Second Embodiment

In a second embodiment, the same configurations as those in the first embodiment have the same reference characters, description of the contents that overlap with those in the first embodiments is omitted or simplified, and contents different from those in the first embodiment will be primarily described.

1-2-1. Configuration of Swing Diagnosis System

Figure 20:
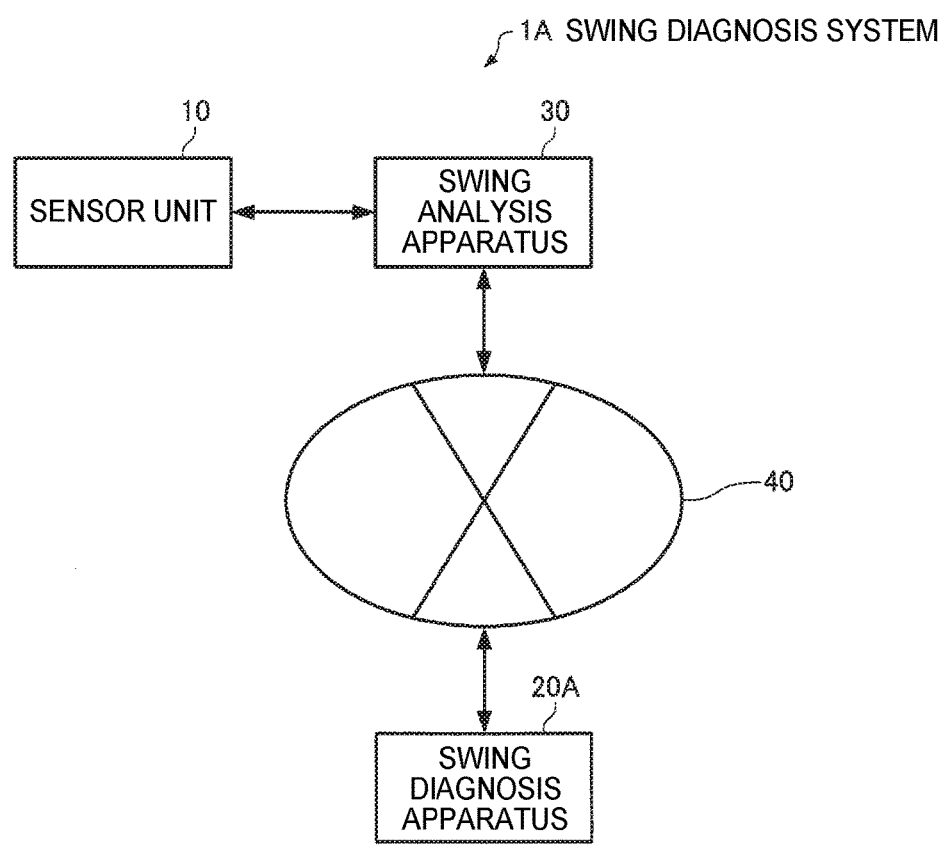
FIG. 20 shows an example of the configuration of a swing diagnosis system according to a second embodiment.

FIG. 20 shows an example of the configuration of a swing diagnosis system according to the second embodiment. A swing diagnosis system 1A according to the second embodiment includes the sensor unit 10, a swing analysis apparatus 30, and a swing diagnosis apparatus 20A, as shown in FIG. 20.

When the user 2 performs the measurement start operation in step S2 in FIG. 3, the swing analysis apparatus 30 transmits a measurement start command to the sensor unit 10, and the sensor unit 10 receives the measurement start command and starts measurement of the three-axis acceleration and the three-axis angular velocity. The communication between the sensor unit 10 and the swing analysis apparatus 30 may be wireless communication or wired communication.

The swing analysis apparatus 30 notifies the user 2 of the swing start permission shown in step S5 in FIG. 3 and then analyzes the swing action in which the user 2 used the golf club 3 to hit a ball (step S6 in FIG. 3).

The swing analysis apparatus 30 then generates swing analysis data containing the time (date and hour) when the swing was performed, identification information on the user and the user's gender, the type of the golf club 3, information on a result of the analysis of the swing action and transmits the swing analysis data to the swing diagnosis apparatus 20A over a network 40 (see FIG. 20).

The swing diagnosis apparatus 20A receives and saves the swing analysis data transmitted from the swing analysis apparatus 30 over the network 40. Therefore, whenever the user 2 performs swing action in accordance with the procedure in FIG. 3, the swing analysis data generated by the swing analysis apparatus 30 is saved in the swing diagnosis apparatus 20A, and a swing analysis data list is constructed.

The swing analysis apparatus 30 may be implemented, for example, in the form of a smartphone, a personal computer, or any other information terminal (client terminal), and the swing diagnosis apparatus 20A may be implemented in the form of a server that processes a request from the swing analysis apparatus 30.

The network 40 may be the Internet or any other wide area network (WAN) or may be a local area network (LAN). Instead, the swing analysis apparatus 30 and the swing diagnosis apparatus 20A may not communicate with each other over the network 40 but may communicate with each other, for example, in short-distance wireless communication or wired communication.

In the present embodiment, when the user 2 activates a swing diagnosis application program via the operation section 23 (see FIG. 21) of the swing analysis apparatus 30, the swing analysis apparatus 30 communicates with the swing diagnosis apparatus 20A, and a swing analysis data selection screen is displayed in the display section 25 of the swing analysis apparatus 30. The selection screen contains a list of the swing analysis data on the swing of the user 2 contained in the swing analysis data list saved in the swing diagnosis apparatus 20A. The user operates the swing analysis apparatus 30 to select any of the swing analysis data from the swing analysis data list. The swing analysis apparatus 30 thus transmits information on the selection of the swing analysis data to the swing diagnosis apparatus 20A.

The swing diagnosis apparatus 20A receives the selection information and uses the selected swing analysis data to calculate the scores of the predetermined items. Specifically, the swing diagnosis apparatus 20A calculates the scores of the two items, "the V zone" and "the speed," for example, in the scale of 5, as in the first embodiment. The swing diagnosis apparatus 20A may further calculate the overall score of the swing on the basis of the scores of the two items. The swing diagnosis apparatus 20A then transmits information on the calculated scores of the predetermined items and the calculated overall score to the swing analysis apparatus 30.

The swing analysis apparatus 30 receives the information on the scores of the predetermined items and the overall score and causes the display section 25 to display the swing diagnosis screen shown in FIG. 6. The user 2 looks at the swing diagnosis screen in FIG. 6 and can grasp the scores of the plurality of items and the overall score as a result of the diagnosis of the swing analysis data on the left. In particular, the user 2 can grasp a strong point and a weak point of the swing of the user from the swing diagnosis screen in FIG. 6.

1-2-2. Configurations of Sensor Unit and Swing Analysis Apparatus

Figure 21:
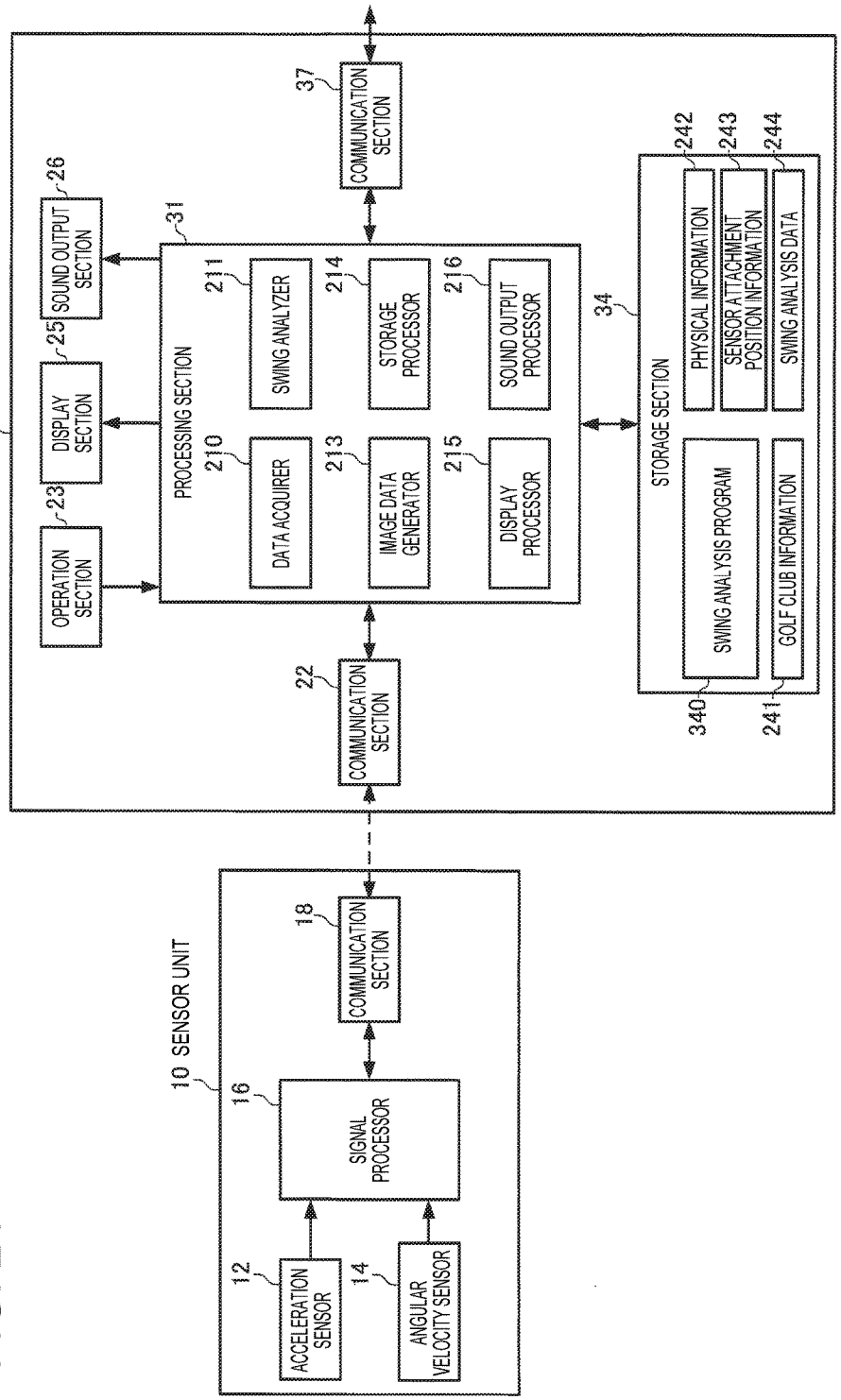
FIG. 21 shows an example of the configurations of a sensor unit and a swing analysis apparatus in the second embodiment.

FIG. 21 shows an example of the configurations of the sensor unit 10 and the swing analysis apparatus 30. The configuration and function of the sensor unit 10 are the same as those in the first embodiment, as shown in FIG. 21, and no description thereof will therefore be made.

The swing analysis apparatus 30 includes a processing section 31, the communication section 22, the operation section 23, a storage section 34, the display section 25, the sound output section 26, and a communication section 37. It is, however, noted that the swing analysis apparatus 30 may have a configuration in which part of the components described above is deleted or changed as appropriate or another component is added as appropriate. The configurations and functions of the communication section 22, the operation section 23, the display section 25, and the sound output section 26 are the same as those in the first embodiment, and no description thereof will therefore be made.

The storage section 34 is formed, for example, of a ROM, a flash ROM, a RAM, or any of a variety of IC memories, a hard disk drive, a memory card, or any other recording medium, or any other components. The storage section 34 stores programs used by the processing section 31 to carry out a variety of calculation processes and control processes, a variety of programs and data for achieving application functions, and other pieces of information.

In the present embodiment, the storage section 34 stores a swing analysis program 340 read by the processing section 31 for the swing analysis. The swing analysis program 340 may be stored in a nonvolatile recording medium (computer readable recording medium) in advance, or the processing section 31 may receive the swing analysis program 340 from a server that is not shown over a network or the swing diagnosis apparatus 20A and store the swing analysis program 340 in the storage section 34.

The storage section 34 further stores the golf club information 241, the physical information 242, the sensor attachment position information 243, and the swing analysis data 244.

The storage section 34 is further used as a work area by the processing section 31 and temporarily stores data acquired via the operation section 23, results of computation performed by the processing section 31 in accordance with a variety of programs, and other pieces of information. The storage section 34 may further store data required to be saved for a long period among data generated in the processes carried out by the processing section 31.

The communication section 37 performs data communication with a communication section 27 (see FIG. 22) of the swing diagnosis apparatus 20A over the network 40. For example, after the swing analysis is completed, the communication section 37 receives the swing analysis data 244 from the processing section 31 and transmits the swing analysis data 244 to the communication section 27 of the swing diagnosis apparatus 20A. Further, for example, the communication section 37 carries out the process of receiving information required to display the swing analysis data selection screen via the communication section 27 of the swing diagnosis apparatus 20A and transmitting the information to the processing section 31 and the process of receiving information on the selection in the selection screen from the processing section 31 and transmitting the selection information to the communication section 27 of the swing diagnosis apparatus 20A. Further, for example, the communication section 37 receives information required to display the swing diagnosis screen shown in FIG. 6 (information on result of diagnosis based on selected swing analysis data (scores of predetermined items and overall score)) via the communication section 27 of the swing diagnosis apparatus 20A and transmits the information to the processing section 31.

The processing section 31 carries out, in accordance with a variety of programs, the process of transmitting the control commands to the sensor unit 10 via the communication section 22 and a variety of types of calculation processes on the data received from the sensor unit 10 via the communication section 22. The processing section 31 further reads the swing analysis data 244 from the storage section 34 and transmits the swing analysis data 244 to the swing diagnosis apparatus 20A via the communication section 37 in accordance with the variety of programs. The processing section 31 further transmits information on the selection of swing analysis data to the swing diagnosis apparatus 20A via the communication section 37, displays the swing diagnosis screen in FIG. 6 on the basis of information received from the swing diagnosis apparatus 20A, and carries out other processes in accordance with the variety of programs. The processing section 31 still further carries out a variety of other control processes.

In particular, in the present embodiment, the processing section 31 executes the swing analysis program 340 to function as the data acquirer 210, the swing analyzer 211, the image data generator 213, the storage processor 214, the display processor 215, and the sound output processor 216 and analyzes the swing action of the user 2 (swing analysis). The configurations and functions of the data acquirer 210, the swing analyzer 211, the image data generator 213, the storage processor 214, the display processor 215, and the sound output processor 216 are the same as those in the first embodiment, and no description thereof will therefore be made. Further, the swing analysis is the same as that in the first embodiment, and no description thereof will therefore be made.

1-2-3. Configuration of Swing Diagnosis Apparatus

Figure 22:
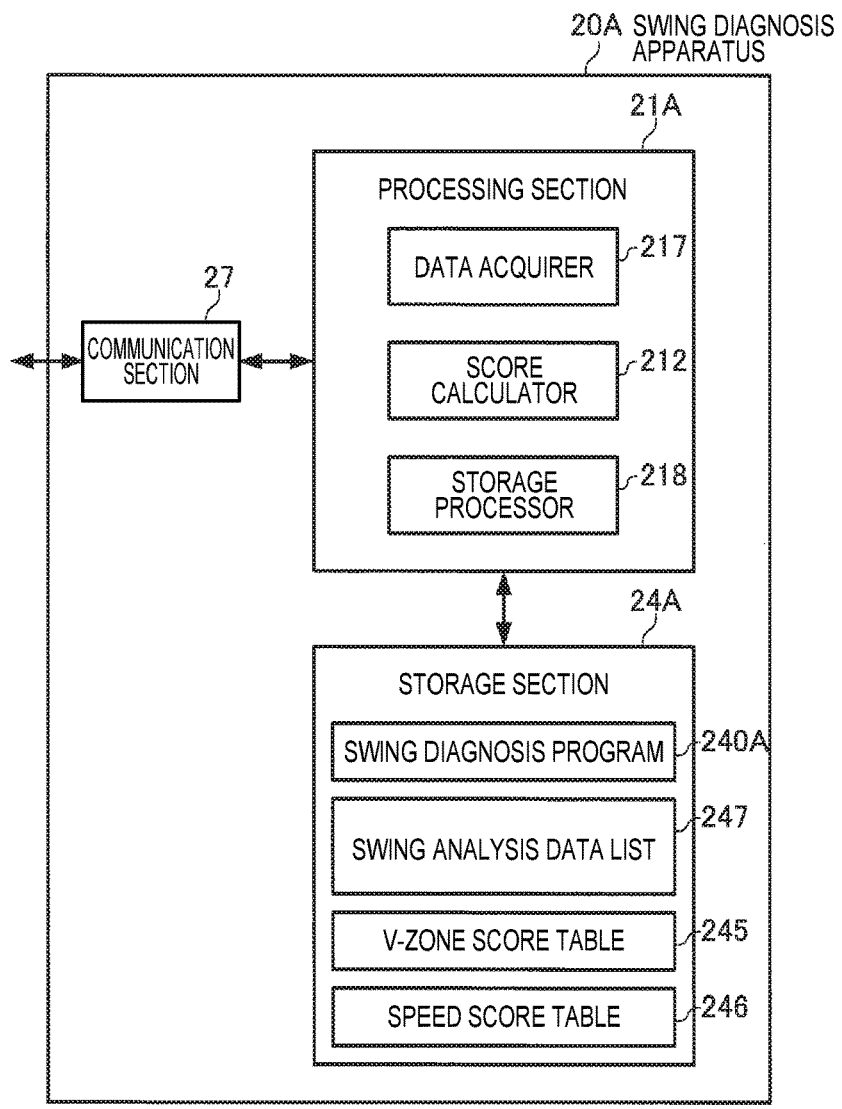
FIG. 22 shows an example of the configuration of a swing diagnosis apparatus in the second embodiment.

FIG. 22 shows an example of the configuration of the swing diagnosis apparatus 20A. In the present embodiment, the swing diagnosis apparatus 20A includes a processing section 21A, the communication section 27, and a storage section 24A, as shown in FIG. 22. It is, however, noted that the swing diagnosis apparatus 20A may have a configuration in which part of the components described above is deleted or changed as appropriate or another component is added as appropriate.

The storage section 24A is formed, for example, of a ROM, a flash ROM, a RAM, or any of a variety of IC memories, a hard disk drive, a memory card, or any other recording medium, or any other components. The storage section 24A stores programs used by the processing section 21A to carry out a variety of calculation processes and control processes, a variety of programs and data for achieving application functions, and other pieces of information.

In the present embodiment, the storage section 24A stores a swing diagnosis program 240A read by the processing section 21A for the swing diagnosis. The swing diagnosis program 240A may be stored in a nonvolatile recording medium (computer readable recording medium) in advance, or the processing section 21A may receive the swing diagnosis program 240A from a server that is not shown over a network and store the swing diagnosis program 240A in the storage section 24A.

Further, in the present embodiment, the storage section 24A stores (saves) a swing analysis data list 247 containing a plurality of sets of swing analysis data 244 generated by the swing analysis apparatus 30. That is, the swing analysis data 244 generated whenever the processing section 31 of the swing analysis apparatus 30 analyzes a swing action of the user 2 is successively added to the swing analysis data list 247.

In the present embodiment, the storage section 24A further stores the V-zone score table 245 and the speed score table 246.

The storage section 24A is further used by the processing section 21A as a work area and temporarily stores results of computation performed by the processing section 21A in accordance with a variety of programs and other pieces of information. The storage section 24A may further store data required to be saved for a long period among data generated in the processes carried out by the processing section 21A.

The communication section 27 performs data communication with the communication section 37 (see FIG. 21) of the swing analysis apparatus 30 over the network 40. For example, the communication section 27 receives the swing analysis data 244 via the communication section 37 of the swing analysis apparatus 30 and transmits the swing analysis data 244 to the processing section 21A. Further, for example, the communication section 27 carries out the process of transmitting information required to display the swing analysis data selection screen to the communication section 37 of the swing analysis apparatus 30 and the process of receiving information on the selection in the swing analysis data selection screen via the communication section 37 and transmitting the selection information to the processing section 21A. Further, for example, the communication section 27 receives information on a result of the diagnosis based on the swing analysis data 244 selected in accordance with the selection information (scores of predetermined items and overall score) from the processing section 21A and transmits the information to the communication section 37 of the swing analysis apparatus 30. Further, for example, the communication section 27 receives information required to display the swing diagnosis screen in FIG. 6 from the processing section 21A and transmits the information to the communication section 37 of the swing analysis apparatus 30.

The processing section 21A receives the swing analysis data 244 from the swing analysis apparatus 30 via the communication section 27 and stores the swing analysis data 244 in the storage section 24A (adds swing analysis data 244 to swing analysis data list 247) in accordance with a variety of programs. The processing section 21A further receives the selection information from the swing analysis apparatus 30 via the communication section 27, transmits information required to display the swing diagnosis screen in FIG. 6 to the swing analysis apparatus 30, and carries out other processes. The processing section 21A further carries out a variety of other control processes.

In particular, in the present embodiment, the processing section 21A executes the swing diagnosis program 240A to function as a data acquirer 217, the score calculator 212, and a storage processor 218 and performs diagnosis of the swing analysis data 244 selected from the swing analysis data list 247 (swing diagnosis).

The data acquirer 217 receives the swing analysis data 244 received from the swing analysis apparatus 30 via the communication section 27 and transmits the swing analysis data 244 to the storage processor 218. The data acquirer 217 further receives a variety of pieces of information received from the swing analysis apparatus 30 via the communication section 27 and transmits the information to the score calculator 212.

The storage processor 218 reads/writes a variety of programs and a variety of data from and to the storage section 24A. For example, the storage processor 218 receives the swing analysis data 244 from the data acquirer 217 and stores the swing analysis data 244 in the storage section 24A (add swing analysis data 244 to swing analysis data list 247) and reads the swing analysis data 244 from the swing analysis data list 247 stored in the storage section 24A. Further, for example, the storage processor 218 reads the V-zone score table 245 and the speed score table 246 stored in the storage section 24A.

The score calculator 212 calculates the scores of the predetermined items on the basis of data on a swing. In the present embodiment, the data on the swing is the swing analysis data 244 selected on the basis of the selection information. The function of the score calculator 212 and the score calculation performed by the score calculator 212 are the same as those in the first embodiment, and no description thereof will therefore be made.

1-2-4. Procedure of Swing Diagnosis (Swing Diagnosis Method)

Figure 23:
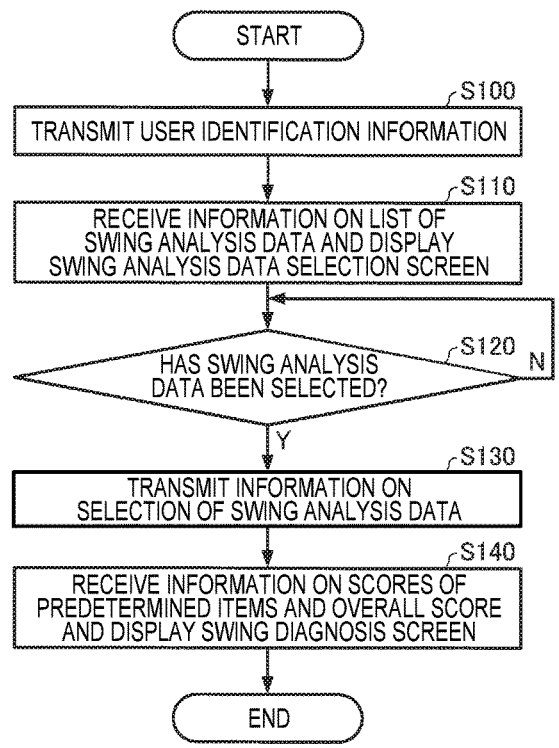
FIG. 23 is a flowchart showing an example of the procedure of a swing diagnosis-related process carried out by the swing analysis apparatus in the second embodiment.
Figure 24:
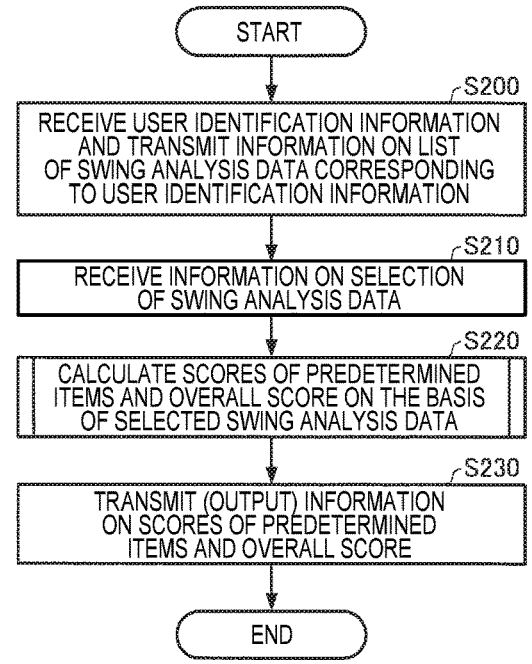
FIG. 24 is a flowchart showing an example of the procedure of the swing diagnosis process (swing diagnosis method) in the second embodiment.

FIG. 23 is a flowchart showing an example of the procedure of a swing-diagnosis-related process carried out by the processing section 31 of the swing analysis apparatus 30. FIG. 24 is a flowchart showing an example of the procedure of the swing diagnosis (swing diagnosis method) performed by the processing section 21A of the swing diagnosis apparatus 20A. The processing section 21A (example of computer) of the swing diagnosis apparatus 20A executes the swing diagnosis program 240A stored in the storage section 24A to perform the swing diagnosis, for example, in accordance with the procedure in the flowchart of FIG. 24. The flowcharts of FIGS. 23 and 24 will be described below.

The processing section 31 of the swing analysis apparatus 30 first transmits user identification information assigned to the user 2 (S100 in FIG. 23).

The processing section 21A of the swing diagnosis apparatus 20A then receives the user identification information and transmits information on the list of the swing analysis data 244 corresponding to the user identification information (S200 in FIG. 24).

The processing section 31 of the swing analysis apparatus 30 then receives the information on the list of the swing analysis data 244 and causes the display section 25 to display the swing analysis data selection screen (S110 in FIG. 23).

The processing section 31 of the swing analysis apparatus 30 then waits until swing analysis data 244 is selected in the swing analysis data selection screen (N in S120 in FIG. 23). When swing analysis data 244 is selected (Y in S120 in FIG. 23), the processing section 31 transmits information on the selection of swing analysis data to the swing diagnosis apparatus 20A (S130 in FIG. 23).

The processing section 21A of the swing diagnosis apparatus 20A then receives the information on the selection of swing analysis data (S210 in FIG. 24) and calculates the scores of the predetermined items and the overall score on the basis of the swing analysis data 244 selected on the basis of the selection information (S220 in FIG. 24). The detailed procedure of step S220 is the same as the procedure in FIG. 19.

The processing section 21A of the swing diagnosis apparatus 20A then transmits (outputs) information on the scores of the predetermined items and the overall score to the swing analysis apparatus 30 (S230 in FIG. 24) and terminates the swing diagnosis.

The processing section 31 of the swing analysis apparatus 30 then receives the information on the scores of the predetermined items and the overall score, causes the display section 25 to display the swing diagnosis screen (FIG. 6) (S140 in FIG. 23), and terminates the process.

In the flowchart of FIG. 23, the order of the steps may be changed as appropriate to the extent possible, part of the steps may be deleted or changed, or another step may be added. Similarly, in the flowchart of FIG. 24, the order of the steps may be changed as appropriate to the extent possible, part of the steps may be deleted or changed, or another step may be added.

1-2-5. Advantageous Effects

As described above, in the swing diagnosis system 1A according to the second embodiment, the swing analysis apparatus 30 uses measured data from the sensor unit 10 to generate swing analysis data 244. The swing diagnosis apparatus 20A calculates scores on the basis of the selected swing analysis data 244 and on the basis of the relationship between the imaginary planes and the positions of the head of the golf club 3 at desired timings during the backswing and during the downswing. The swing analysis apparatus 30 can then display the scores calculated by the swing diagnosis apparatus 20A in the display section 25 for clear visual recognition of the characteristics of the swing up to the impact in the form of numerals.

Further, according to the swing diagnosis system 1A of the second embodiment, the score of the item "V zone" can be used to clearly show the characteristics of the swing in the form of numerals on the basis of the relationship among the shaft plane SP (first imaginary plane), the Hogan plane HP (second imaginary plane), and the positions of the head of the golf club 3 at desired timings during the backswing and during the downswing (halfway back state and halfway down state), as in the swing diagnosis system 1 of the first embodiment.

Further, according to the swing diagnosis system 1A of the second embodiment, the score of the item "speed" can be used to clearly show the characteristics of the swing in the form of numerals on the basis of the speed of the head of the golf club 3 at the impact, as in the swing diagnosis system 1 of the first embodiment.

The user 2 can therefore grasp the level of the swing, a strong point and a weak point of the swing, a problem with the swing, and other pieces of information from the score of the item "V zone" and the score of the item "speed" obtained as a result of the diagnosis based on the swing analysis data 244.

Moreover, according to the swing diagnosis system 1A of the second embodiment, since the swing diagnosis apparatus 20A performs the swing diagnosis (score calculation), the burden on the swing analysis apparatus 30 can be reduced.

Further, according to the swing diagnosis system 1A of the second embodiment, the same advantageous effects as those provided by the swing diagnosis system 1 of the first embodiment can be provided.

2. Variations

The invention is not limited to the embodiment described above, and a variety of variations are conceivable in the scope of the substance of the invention.

2-1. Swing Diagnosis System

In the second embodiment described above, the swing diagnosis apparatus 20A may carry out part of the processes carried out by the swing analysis apparatus 30 (swing analysis), or the swing analysis apparatus 30 may carry out part of the processes carried out by the swing diagnosis apparatus 20A (swing diagnosis).

In the second embodiment described above, the swing diagnosis system 1A may be so configured as to include a plurality of sensor units 10 and a plurality of swing analysis apparatus 30.

2-2. Swing Analysis

A plurality of sensor units 10 may be attached to the golf club 3 and an arm, a shoulder, or any other portion of the user 2, and the swing analyzer 211 may use measurement data from each of the plurality of sensor units 10 to perform the swing analysis.

In each of the embodiments described above, the swing analyzer 211 uses the physical information on the user 2 to calculate the third line segment 53, which is the third axis, and the Hogan plane HP. Instead, the second segment 52, which is the second axis, and the shaft plane SP may be rotated around the X axis by a predetermined first angle β (30°, for example), and the rotated second segment and the shaft plane may be used as the third line segment 53 and the Hogan plane HP.

In the embodiments described above, the swing analyzer 211 uses the square root of the sum of squares, such as those shown by Expression (2), as the combined value of the three-axis angular velocity measured with the sensor unit to detect the impact. In place of the sum of squares described above, for example, the sum of squares of the three-axis angular velocity, the sum of the three-axis angular velocity or the average thereof, or the product of the three-axis angular velocity may be used as the combined value of the three-axis angular velocity. Still instead, in place of the combined value of the three-axis angular velocity, a combined value of the three-axis acceleration, such as the sum of squares of the three-axis acceleration or the square root thereof, the sum of the three-axis acceleration or the average thereof, or the product of the three-axis acceleration, may be used.

2-3. Swing Diagnosis

In each of the embodiments described above, part or entirety of the values of the indices contained in the swing analysis data 244 may be configured to be changeable, and the score calculator 212 may calculate the scores of the predetermined items and the overall score on the basis of data in which part or entirety of the values of indices are changed. Further, the score calculator 212 may calculate the scores of the predetermined items and the overall score on the basis of data in which the entirety of the values of the indices representing the characteristics of a swing are pseudo values (data in which all indices are manually inputted, for example).

In the embodiments described above, the score calculator 212 calculates the scores of the two items, "the V zone" and "the speed," but the score of the item "speed" may not be calculated, or the score of another item may be calculated. Further, in each of the embodiments described above, the score calculator 212 calculates the overall score, but the overall score may not be calculated.

In the embodiments described above, the score calculator 212 may calculate the scores on the basis of the relationship between one imaginary plane and the positions of the head of the golf club 3 at desired timings during the backswing and during the downswing. The imaginary plane may be the shaft plane SP, the Hogan plane HP, or any other flat plane (for example, a flat plane between the shaft plane SP and the Hogan plane HP, a flat plane outside the shaft plane SP and the Hogan plane HP, and a flat plane that intersects at least one of the shaft plane SP and the Hogan plane HP). For example, the score calculator 212 may calculate one or more boundary planes each inclined with respect to the imaginary plane by a predetermined angle and set a plurality of areas for classification of the position of the head of the golf club 3.

In each of the embodiments described above, the score calculator 212 uses the score tables to calculate the scores of the predetermined items, but a numeral expression may be used in place of the score tables.

In each of the embodiments described above, the score calculator 212 may also function as the swing analyzer 211 to perform the swing diagnosis including the swing analysis (swing analysis and score calculation) on the basis of measured data, which is data on a swing, from the sensor unit 10 (output signal from inertial sensor).

2-4. Others

In each of the embodiments described above, the acceleration sensor 12 and the angular velocity sensor 14 are built in and integrated with the sensor unit 10, but the acceleration sensor 12 and the angular velocity sensor 14 may not be integrated with the sensor unit 10. Instead, the acceleration sensor 12 or the angular velocity sensor 14 may not be built in the sensor unit 10, but the acceleration sensor 12 and the angular velocity sensor 14 may be directly attached to the golf club 3 or the user 2. Further, in each of the embodiments described above, the sensor unit 10 and the swing diagnosis apparatus 20 or the swing analysis apparatus 30 are separate members, but they may be integrated with each other, and the integrated unit may be configured to be attachable to the golf club 3 or the user 2. Instead, the sensor unit 10 may include not only the inertial sensor (acceleration sensor 12 or angular velocity sensor 14, for example) but also part of the components that form the swing diagnosis apparatus 20 or the swing analysis apparatus 30.

Each of the embodiments described above has been described with reference to a swing diagnosis system (swing diagnosis apparatus) that diagnoses a golf swing, and the invention is applicable to a swing diagnosis system (swing diagnosis apparatus) that diagnoses swings in a variety of sports, such as tennis and baseball.

The embodiments and variations described above are presented by way of example, and the invention is not limited thereto. For example, any of the embodiments and the variations may be combined with each other as appropriate.

The invention encompasses substantially the same configuration as the configuration described in each of the embodiments (for example, a configuration having the same function, using the same method, and providing the same result or a configuration having the same purpose and providing the same effect). Further, the invention encompasses a configuration in which an inessential portion of the configuration described in each of the embodiments is replaced. Moreover, the invention encompasses a configuration that provides the same advantageous effect as that provided by the configuration described in each of the embodiments or a configuration that can achieve the same purpose as that achieved by the configuration described in each of the embodiments. Further, the invention encompasses a configuration in which a known technology is added to the configuration described in each of the embodiments.

The entire disclosure of Japanese Patent Application No. 2015-148638 filed Jul. 28, 2015 is expressly incorporated by reference herein.

What is claimed is:

1. A swing diagnosis apparatus comprising:
a processor programmed to:
define a plurality of areas by at least one imaginary plane identified by a target direction of a hit ball during a time of an address;
detect a first position of a hitting section of a sport gear at a first timing during a backswing;
detect a second position of the hitting section at a second timing during a downswing;
determine to which one of the plurality of areas the first position and the second position belong;
calculate a tentative score based on the determination to which one of the plurality of areas the first position and the second position belong; and
calculate an overall score by adjusting the tentative score based on a speed of the hitting section.

2. The swing diagnosis apparatus according to claim 1, wherein:
the at least one imaginary plane includes a first imaginary plane identified based on (i) a first axis along the target direction of the hit ball, and (ii) a second axis along a longitudinal direction of the sport gear before the backswing starts.

3. The swing diagnosis apparatus according to claim 1, wherein:
the at least one imaginary plane includes a second imaginary plane identified based on (i) a first axis along the target direction of the hit ball, and (ii) a third axis inclined with respect to a longitudinal direction of the sport gear by a first angle before the backswing starts.

4. The swing diagnosis apparatus according to claim 1, wherein the processor is programmed to calculate the overall score based on a degree of curvature of an expected hit ball.

5. The swing diagnosis apparatus according to claim 1, wherein:
the first timing is a point in time when a longitudinal direction of the sport gear coincides with a direction along a horizontal direction during the backswing; and
the second timing is a point in time when the longitudinal direction of the sport gear coincides with the direction along the horizontal direction during the downswing.

6. The swing diagnosis apparatus according to claim 1, wherein the speed of the hitting section is measured at a time of an impact.

7. The swing diagnosis apparatus according to claim 1, further comprising:
a display that displays the calculated overall score.

8. A swing diagnosis system comprising:
the swing diagnosis apparatus according to claim 1; and
an inertial sensor,
wherein the processor is programmed to calculate the tentative score based on an output from the inertial sensor.

9. A swing diagnosis method comprising:
defining a plurality of areas by at least one imaginary plane identified by a target direction of a hit ball during a time of an address;
detecting a first position of a hitting section of a sport gear at a first timing during a backswing;
detecting a second position of the hitting section at a second timing during a downswing;
determining to which one of the plurality of areas the first position and the second position belong;
calculating a tentative score based on the determination to which one of the plurality of areas the first position and the second position belong; and
calculating an overall score by adjusting the tentative score based on a speed of the hitting section.

10. The swing diagnosis method according to claim 9, wherein:
the at least one imaginary plane includes a first imaginary plane identified based on (i) a first axis along the target direction of the hit ball, and (ii) a second axis along a longitudinal direction of the sport gear before the backswing starts.

11. The swing diagnosis method according to claim 9, wherein:
the at least one imaginary plane includes a second imaginary plane identified based on (i) a first axis along the target direction of the hit ball, and (ii) a third axis inclined with respect to a longitudinal direction of the sport gear by a first angle before the backswing starts.

12. The swing diagnosis method according to claim 9, wherein the overall score is calculated based on a degree of curvature of an expected hit ball.

13. The swing diagnosis method according to claim 9, wherein:
the first timing is a point in time when a longitudinal direction of the sport gear coincides with a direction along a horizontal direction during the backswing; and
the second timing is a point in time when the longitudinal direction of the sport gear coincides with the direction along the horizontal direction during the downswing.

14. The swing diagnosis method according to claim 9, wherein the speed of the hitting section is measured at a time of an impact.

15. The swing diagnosis method according to claim 9, further comprising:
displaying the calculated overall score.

16. A non-transitory recording medium that records a swing diagnosis program that causes a computer to perform:
defining a plurality of areas by at least one imaginary plane identified by a target direction of a hit ball during a time of an address;
detecting a first position of a hitting section of a sport gear at a first timing during a backswing;
detecting a second position of the hitting section at a second timing during a downswing;
determining to which one of the plurality of areas the first position and the second position belong;
calculating a tentative score based on the determination to which one of the plurality of areas the first position and the second position belong; and calculating an overall score by adjusting the tentative score based on a speed of the hitting section.

17. A swing diagnosis apparatus that:
defines a plurality of areas by at least one imaginary plane identified by a target direction of a hit ball during a time of an address;
detects a first position of a hitting section of a sport gear at a first timing during a backswing;
detects a second position of the hitting section at a second timing during a downswing;
determines to which one of the plurality of areas the first position and the second position belong;
calculates a tentative score based on the determination to which one of the plurality of areas the first position and the second position belong; and
calculates an overall score by adjusting the tentative score based on a speed of the hitting section.

18. The swing diagnosis apparatus according to claim 17, wherein:
the at least one imaginary plane includes a first imaginary plane identified based on (i) a first axis along the target direction of the hit ball, and (ii) a second axis along a longitudinal direction of the sport gear before the backswing starts.

19. The swing diagnosis apparatus according to claim 17, wherein:
the at least one imaginary plane includes a second imaginary plane identified based on (i) a first axis along the target direction of the hit ball, and (ii) a third axis inclined with respect to a longitudinal direction of the sport gear by a first angle before the backswing starts.

20. The swing diagnosis apparatus according to claim 17, wherein the overall score is calculated based on a degree of curvature of an expected hit ball.

21. The swing diagnosis apparatus according to claim 17, wherein:
the first timing is a point in time when a longitudinal direction of the sport gear coincides with a direction along a horizontal direction during the backswing, and
the second timing is a point in time when the longitudinal direction of the sport gear coincides with the direction along the horizontal direction during the downswing.

22. The swing diagnosis apparatus according to claim 17, wherein the speed of the hitting section is measured at a time of at an impact.

23. The swing diagnosis apparatus according to claim 17, wherein the swing diagnosis apparatus displays the calculated overall score.

* * * * *